(12) United States Patent
Khademhosseini

(10) Patent No.: US 12,329,611 B2
(45) Date of Patent: Jun. 17, 2025

(54) EAR AND NOSE CLEANING DEVICE

(71) Applicant: ND Products, Inc, McLean, VA (US)

(72) Inventor: Nami Khademhosseini, Falls Church, VA (US)

(73) Assignee: ND Products Inc

( * ) Notice: Subject to any disclaimer, the term of this patent is extended or adjusted under 35 U.S.C. 154(b) by 126 days.

(21) Appl. No.: 17/486,408

(22) Filed: Sep. 27, 2021

(65) Prior Publication Data

US 2023/0102609 A1  Mar. 30, 2023

(51) Int. Cl.
*A61F 11/00* (2022.01)
*A61F 13/38* (2006.01)
*A61M 3/02* (2006.01)

(52) U.S. Cl.
CPC ......... *A61F 11/006* (2013.01); *A61M 3/0279* (2013.01); *A61M 2210/0618* (2013.01); *A61M 2210/0662* (2013.01)

(58) Field of Classification Search
CPC ............. A61F 11/006; A61M 3/00279; A61M 2210/0618; A61M 2210/0062
See application file for complete search history.

(56) References Cited

U.S. PATENT DOCUMENTS

| | | | |
|---|---|---|---|
| 10,813,792 B2 | 10/2020 | Khademhosseini | |
| 2009/0012424 A1* | 1/2009 | Huschmand Nia | A61B 10/0045 600/569 |
| 2016/0256327 A1* | 9/2016 | Kim | A61F 13/38 |
| 2016/0302973 A1* | 10/2016 | Kraitzer | A61M 31/00 |
| 2016/0361203 A1* | 12/2016 | Khademhosseini | A61M 1/85 |
| 2019/0143029 A1* | 5/2019 | Diwan | A61M 3/0275 606/162 |

FOREIGN PATENT DOCUMENTS

CN  203017177 U  *  6/2013

OTHER PUBLICATIONS

U.S. Appl. No. 29/226,287, filed Jun. 26, 2007, Khademhosseini.

* cited by examiner

*Primary Examiner* — Anh T Dang
(74) *Attorney, Agent, or Firm* — IP Consulting Group; Michael Razavi; Alfred F Hoyte, Jr.

(57) ABSTRACT

The present invention discloses an ear and/or nose cleaning device comprising a handle including at least one cartridge. The cleaning device further comprises at least one cleaning tip having a spiral body, at least one curved shape feature, a set of bristles, or a combination thereof. The spiral body can include one of an oval shape arrangement and a cylindrical shape arrangement. The handle is configured to couple with the at least one cleaning tip using a connection mechanism. Furthermore, the present invention also discloses the cleaning tip for use in an ear and nose cleaning device.

10 Claims, 35 Drawing Sheets

140

140

120A  120B  120C

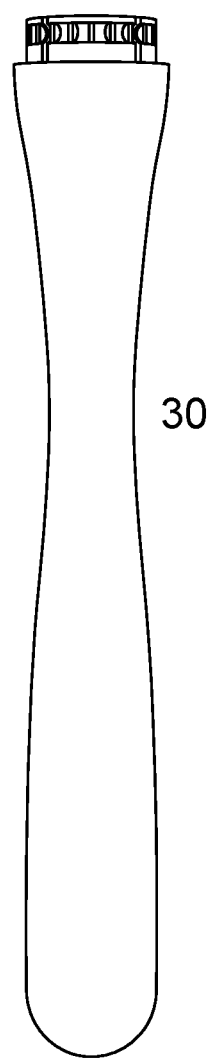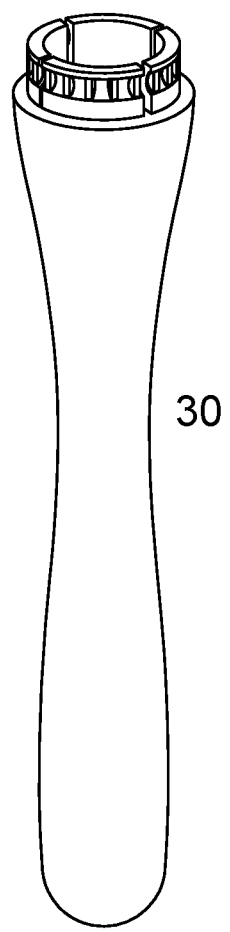
FIG. 25A
FIG. 25B

EAR AND NOSE CLEANING DEVICE

FIELD OF THE INVENTION

The present invention relates to an ear and/or nose cleaning device for cleaning the ear and/or nose of cerumen contaminants, dust, mucus, and particulates. The invention enables a user to perform a proper ear and/or nose cleaning at home without the need of visiting a doctor/professional for ear and/or nose cleaning.

BACKGROUND OF THE INVENTION

Ear and nose cleaning plays a significant role in impacting the overall health of an individual. Many people schedule frequent visits to a doctor for regular checkups and cleaning operations. Although many devices have been developed over the years for such purposes, it is necessary to provide and improve existing ear and nose cleaning devices for ensuring satisfactory cleaning results. This prevents any side effects and injuries that can be caused by improper or hazardous ear and nose cleaning practices that can compromise one's health.

In the case of ear cleaning, the ear canal in human produce cerumen, also known as "earwax", in outer part of the ear canal. The use of audio and mobile device's ear buds, hearing aid buds, or sound protector ear plugs can push the earwax deeper into the ear canal, in which case it can cause many complications, such as reduction of hearing, due to earwax impaction that may cause plague in the ear canal. Cerumen Impaction (Earwax Buildup and Blockage) is a major problem for many people. Regular Q-tip or cotton swab may usually push the earwax further in, blocking and possibly damaging the ear or reduce hearing. Similarly, when a person become congested, particularly with mucus blocking their nasal passage, they can suffer some difficulty and discomfort in breathing, and the problem may become even more severe if the mucus becomes dried and lodged in the nostrils. In case of children, a parent may try to ease this discomfort by helping the child to blow his/her nose or by attempting to clear the child's nostrils. This attempt may not always be successful. There is therefore a need for an effective and safe device for use in clearing the ear canal and nostrils.

Additionally, it is known to use cotton buds/swabs to clear an orifice such as the ear or nose. However, there is a risk of inserting the bud too deep, and /or pushing ear wax deeper as it is not an effective tool for removing particulates/debris, particularly harder ones which do not freely attach to the bud/swab.

Therefore, a need has arisen for an easy-to-use ear and nose cleaning device that is configured to address one or more of the above-mentioned disadvantages/problems and improve the overall health and hygiene of a user by enhancing the effectiveness and user satisfaction of such ear and nose cleaning devices.

SUMMARY OF THE INVENTION

Specific embodiment(s) of the present invention disclosed herein relate to an ear and nose cleaning device. The ear and nose cleaning device comprises a handle including at least one cartridge; and at least one cleaning tip having a spiral body, at least one curved shape feature, a set of bristles, or a combination thereof. Furthermore, the handle is configured to couple with the at least one cleaning tip using a connection mechanism.

In specific embodiment(s) of the invention, the curved shape feature can be a concave shape feature disposed at a distal end of the cleaning tip to facilitate cleaning.

In specific embodiment(s) of the invention, the curved shape feature can be a curette shape feature disposed at a distal end of the cleaning tip to facilitate cleaning.

In specific embodiment(s) of the invention, the spiral body can include an oval shape arrangement. The oval shape arrangement can act as a stopper to prevent excessive insertion of the cleaning device into ear or nose of a user.

In specific embodiment(s) of the invention, the spiral body can include a cylindrical shape arrangement.

In specific embodiment(s) of the invention, the at least one cartridge can be configured to hold and dispense a fluid/composition that facilitates cleaning.

In specific embodiment(s) of the invention, the at least one cartridge can be configured to store one or more cleaning tips.

In specific embodiment(s) of the invention, the at least one transparent window can be provided on the body of the handle to facilitate handles inside view.

In specific embodiment(s) of the invention, at least one of the cleaning tip, the cartridge and the connection mechanism can be disposable.

In specific embodiment(s) of the invention, the connection mechanism can be configured to form a releasable connection between the handle and the cleaning tip.

In specific embodiment(s) of the invention, the connection mechanism can comprise a first connection interface on the handle and a second connection interface on the cleaning tip to form the releasable connection between the handle and the cleaning tip.

In specific embodiment(s) of the invention, the connection mechanism can comprise a connector to form the releasable connection between the handle and the cleaning tip. The connector can further comprise a third connection interface configured to engage operatively with the handle to form a first connection in a first direction; and a fourth connection interface configured to engage operatively with the cleaning tip to form a second connection in a second direction.

In specific embodiment(s) of the invention, the connector can comprise at least one shaft.

In specific embodiment(s) of the invention, the cleaning device can further comprise a stopper configured to prevent excessive insertion of the cleaning device into ear or nose of a user. In a specific example, the stopper can be optionally adjustable in terms of position and/or size.

In specific embodiment(s) of the invention, the handle can comprise a flat base to stand on a surface.

In specific embodiment(s) of the invention, the handle can comprise a bottom hole for hanging. In specific embodiment(s) of the invention, the handle can include a tapered portion, a ribbed portion, or a combination thereof to provide better grip to a user.

In specific embodiment(s) of the invention, the handle can be configured to operate electronically to dispense a fluid/composition from the at least one cartridge and facilitate cleaning.

In specific embodiment(s) of the invention, the handle can have one end coupled to the cleaning tip having the spiral body and/or the at least one curved shape feature. Additionally, the handle can have other end coupled to the cleaning tip having the set of bristles and/or the at least one curved shape feature.

In specific embodiment(s) of the invention, the handle can comprise a hollow space that acts as the cartridge.

In specific embodiment(s) of the invention, the cleaning tip can include a flexible and/or soft material.

Specific embodiment(s) of the present invention disclosed herein relate to an ear and nose cleaning device. The ear and nose cleaning device comprises a handle including at least one cartridge; and at least one cleaning tip having a spiral body that includes one of an oval shape arrangement and a cylindrical shape arrangement, at least one curved shape feature, or a combination thereof. Furthermore, the handle is configured to couple with the at least one cleaning tip using a connection mechanism.

In specific embodiment(s) of the invention, the curved shape feature can be a concave shape feature disposed at a distal end of the cleaning tip to facilitate cleaning.

In specific embodiment(s) of the invention, the curved shape feature can be a curette shape feature disposed at a distal end of the cleaning tip to facilitate cleaning.

In specific embodiment(s) of the invention, the oval shape arrangement can act as a stopper to prevent excessive insertion of the cleaning device into ear or nose of a user.

In specific embodiment(s) of the invention, the at least one cartridge can be configured to hold and dispense a fluid/composition that facilitates cleaning.

In specific embodiment(s) of the invention, the at least one cartridge can be configured to store one or more cleaning tips.

In specific embodiment(s) of the invention, at least one of the cleaning tips, the cartridge and the connection mechanism can be disposable.

In specific embodiment(s) of the invention, the connection mechanism can be configured to form a releasable connection between the handle and the cleaning tip.

In specific embodiment(s) of the invention, the connection mechanism can comprise a first connection interface on the handle and a second connection interface on the cleaning tip to form the releasable connection between the handle and the cleaning tip.

In specific embodiment(s) of the invention, the connection mechanism can comprise a connector to form the releasable connection between the handle and the cleaning tip. The connector can further comprise a third connection interface configured to engage operatively with the handle to form a first connection in a first direction; and a fourth connection interface configured to engage operatively with the cleaning tip to form a second connection in a second direction.

In specific embodiment(s) of the invention, the connector can comprise at least one shaft.

In specific embodiment(s) of the invention, the cleaning device can further comprise a stopper configured to prevent excessive insertion of the cleaning device into ear or nose of a user. In a specific example, the stopper can be adjustable in terms of position and/or size.

In specific embodiment(s) of the invention, the handle can comprise a flat base to stand on a surface.

In specific embodiment(s) of the invention, the handle can comprise a bottom hole for hanging.

In specific embodiment(s) of the invention, the handle can include a tapered portion, a ribbed portion, or a combination thereof to provide better grip to a user.

In specific embodiment(s) of the invention, the handle can be configured to operate electronically to dispense a fluid/composition from the at least one cartridge and facilitate cleaning.

In specific embodiment(s) of the invention, the handle can have one end coupled to the cleaning tip having the spiral body and/or the at least one curved shape feature. Additionally, the handle can have other end coupled to the cleaning tip having the set of bristles and/or the at least one curved shape feature.

In specific embodiment(s) of the invention, the handle can comprise a hollow space that acts as the cartridge.

In specific embodiment(s) of the invention, the cleaning tip can include a flexible and/or soft material.

Specific embodiment(s) of the present invention disclosed herein relate to a cleaning tip for use in an ear and nose cleaning device. The cleaning tip comprises a spiral body that includes one of an oval shape arrangement and a cylindrical (or conical) shape arrangement, at least one curved shape feature, or a combination thereof. Furthermore, the cleaning tip is configured to couple with a handle of the ear and nose cleaning device using a connection mechanism In specific embodiment(s) of the invention, the curved shape feature can be a concave shape feature disposed at a distal end of the cleaning tip to facilitate cleaning.

In specific embodiment(s) of the invention, the curved shape feature can be a curette shape feature disposed at a distal end of the cleaning tip to facilitate cleaning.

In specific embodiment(s) of the invention, the oval shape arrangement can act as a stopper to prevent excessive insertion of the cleaning device into ear or nose of a user.

In specific embodiment(s) of the invention, the cleaning tip can be configured to form a releasable connection with the handle using the connection mechanism.

In specific embodiment(s) of the invention, the cleaning tip can include a flexible and/or soft material.

In specific embodiment(s) of the invention, function of the stopper is to limit the depth to which the cleaning device can be inserted into a nostril or an ear canal of a user. In a specific example, the size and/or position of the stopper can be adapted/adjusted according to nostril size, ear canal size, or age group of a particular user.

In specific embodiment(s) of the invention, the cleaning device of the present invention can be provided as a set, with multiple handles, cleaning tips, connectors, cartridges, cleaning fluids/compositions and/or stoppers to suit different users or family members according to their respective age, size or medical condition. For example, provisioning of multiple cleaning tips, connectors, cartridges and/or stoppers enable sharing of a same handle of the cleaning device with multiple users. Therefore, different users or family members can connect their respective/individual cleaning tips, cartridges, connectors and/or stoppers to the same handle at different points in time and remove their respective/individual cleaning tips, connectors, cartridges and/or stoppers from the handle after the use in order to share the same handle with multiple users. Advantageously, the cleaning device can be customized to meet specific needs of a user (for example, a child or an adult) according to their respective age, size or medical condition. Advantageous embodiments of the inventive device(s) will be described in the following description by referring to the Figures.

BRIEF DESCRIPTION OF THE DRAWINGS

FIG. 8A and FIG. 8B show the cleaning tip 120 and the handle 110 respectively in the disconnected form. FIG. 8C shows the handle 110 and the cleaning tip 120 connected/coupled to each other without any connector in between.

According to specific embodiment(s) of the present invention.

FIGS. 25A-25B show a side view and a perspective view of another version of the handle 110 with tapered waist 30 according to specific embodiment(s) of the present invention.

DETAILED DESCRIPTION

Figures 1A, 1B, 1C, 1D:
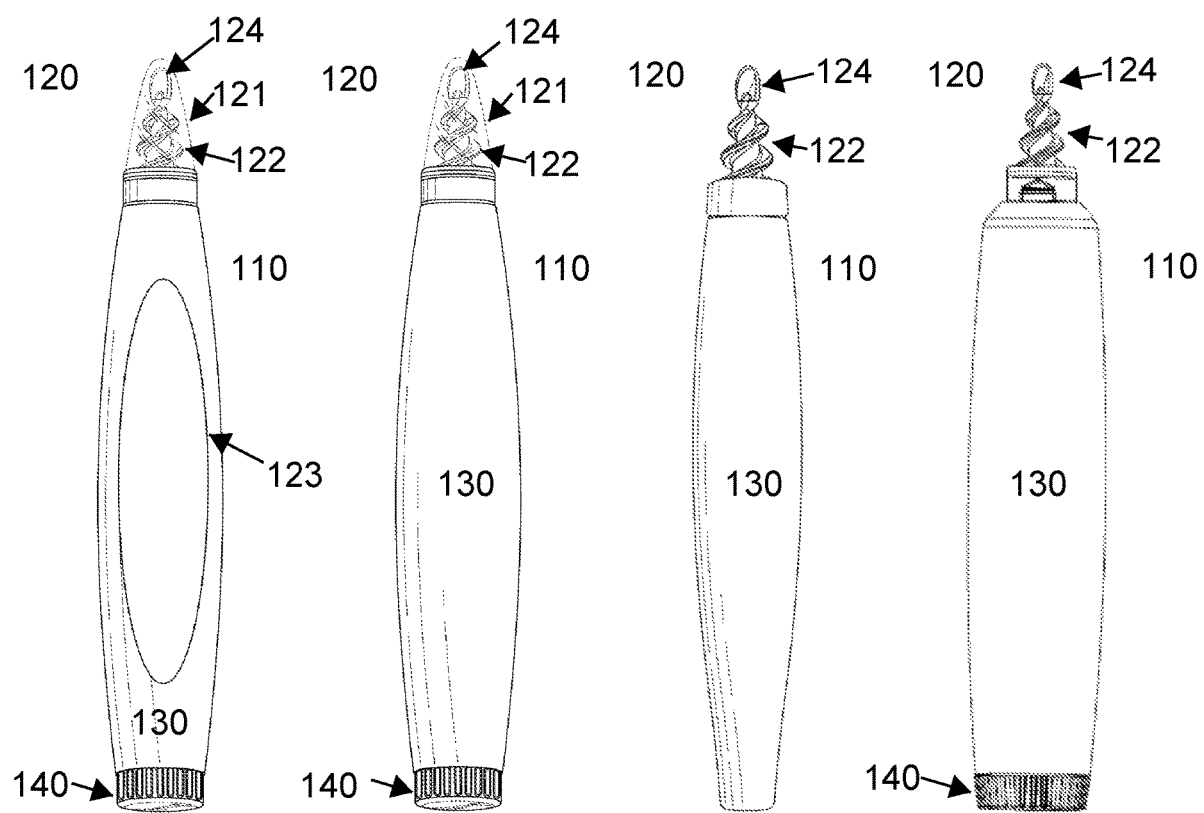
FIGS. 1A-1D, FIGS. 2A-2B and FIG. 3A illustrate 3-D views of an ear and nose cleaning device 100 according to specific embodiment(s) of the present invention.

In the following, features and advantageous embodiments of the present invention will be described in detail with reference to the Figures. Please refer to the drawings in FIGS. I to 32 for some embodiments and variations, with details.

The present invention enables a user to perform a proper ear and/or nose cleaning at home and without the need of visiting a doctor or a professional.

According to an embodiment of the invention, FIG. IA-ID show a 3-D view of different versions of an ear and nose cleaning device I00 comprising of a handle 110 and at least one cleaning tip 120. The handle 110 includes at least one cartridge 130. The cleaning tip 120 may further include a spiral body 122, at least one curved shape feature 124, a set of bristles (not shown in this figure), or a combination thereof. In figures IA-ID, the handle 110 and the cleaning tip 120 are shown together as one piece. Furthermore, the handle 110 and the at least one cleaning tip 120 are configured to arrange/couple using a connection mechanism (described later) in a manner that the cleaning tip 120 is engaged operatively with the handle 110 to form a connection. The ear and nose cleaning device I00 can further comprise of a closure cap 140 at the bottom that can be fixed or openable. In one example, the curved shape feature 124 is a concave shape feature disposed at a distal end of the cleaning tip 120 to facilitate cleaning. In another example, the curved shape feature 124 is a curette shape feature disposed at a distal end of the cleaning tip 120 to facilitate cleaning. As shown in FIGS. IA, IB, and ID, the device 100 may have a thick handle 110. According to another embodiment, the handle 110 of the device I 00 may have a thin ergonomic design. FIG. IA shows an ear and nose cleaning device 100 comprising a top cover 121 and one of more transparent windows 123 in the handle 110. The top cover 121 helps to maintain cleanliness and hygiene of the cleaning tip 120 by preventing deposition of dust and other environmental impurities when the device 100 is not in use. The transparent window 123 provides an inside view of the cartridge 130. According to another embodiment, the handle 110 may be completely opaque and may not have any transparent window as shown in FIGS IB-ID.

According to another embodiment of the invention, the cleaning tip 120 including the spiral body 124 can be a spirally finned tip that excavates, exfoliates removes earwax/nasal deposits, and prevents pushing it further. In one specific example, a user can operate the cleaning device I 00 by spinning the handle 110 in a particular direction (for example, clockwise), as the user proceeds to insert the cleaning tip 120 into the ear canal or a nostril for cleaning and getting the moist out.

According to another embodiment of the invention, the curved shape feature 124 may comprise of bowl shaped or spoon shaped feature for scooping the ear wax or nasal deposits in an efficient manner. The curved shape feature can also be designed to avoid sharp edges on the cleaning tip 120 to avoid possible injury in the ear canal or nostril of a user.

Figure 9:
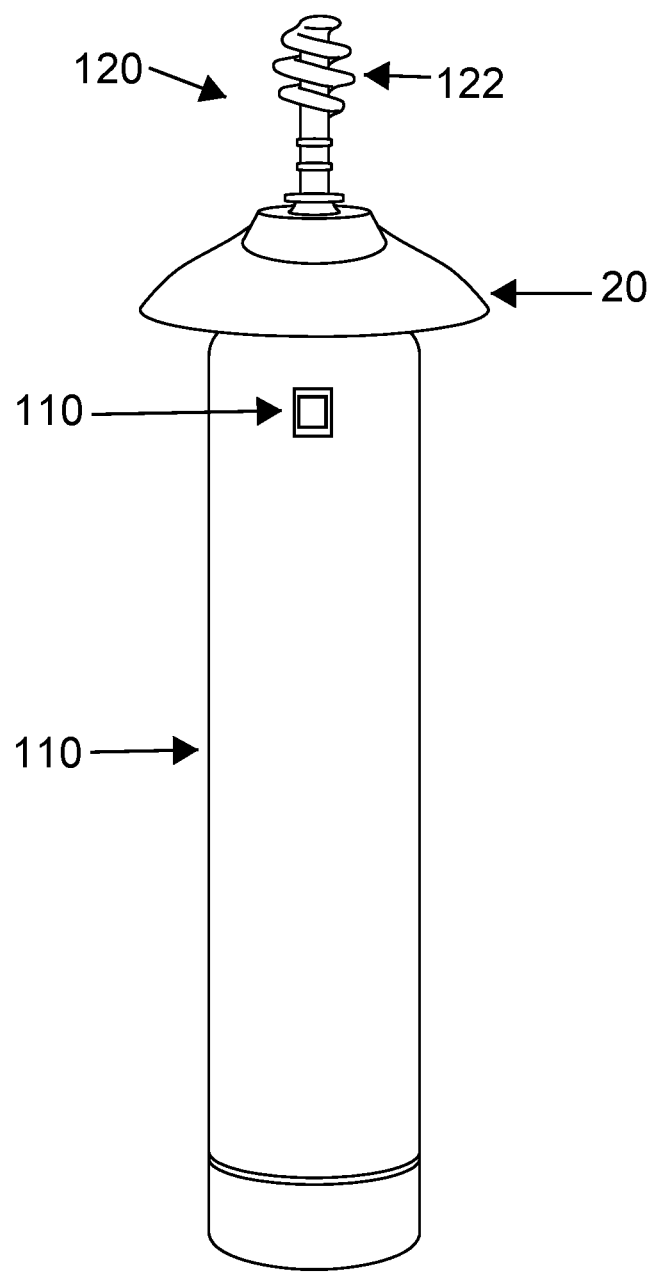
FIG. 9 shows the cleaning device 100 having a stopper 20 according to specific embodiment(s) of the present invention.
Figure 16A:
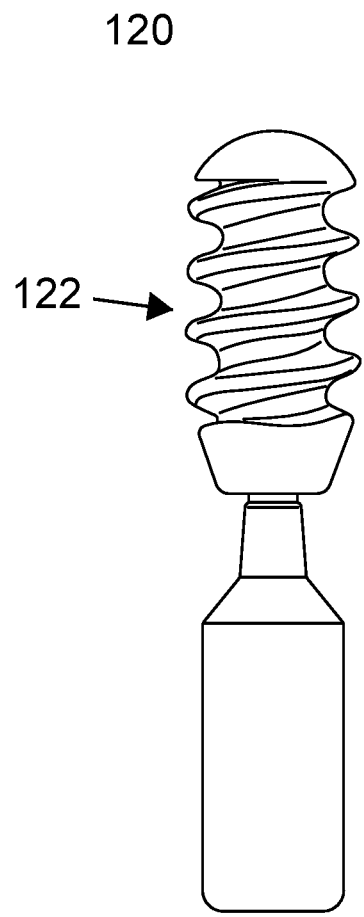
FIG. 16A and FIG. 16B show the cleaning tip 120 having the spiral body 122 in cylindrical shape arrangement according to specific embodiment(s) of the present invention.
Figure 16B:
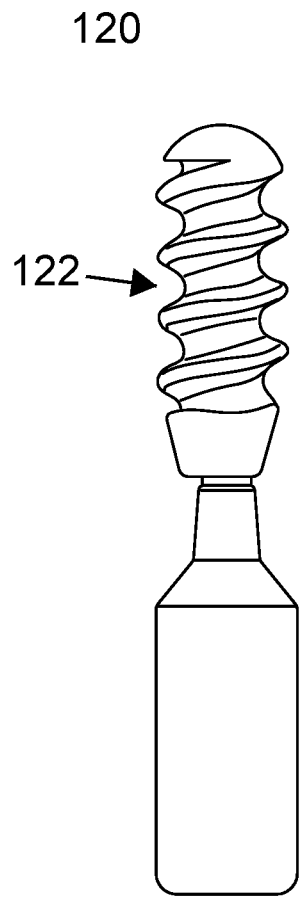
Figure 16C:
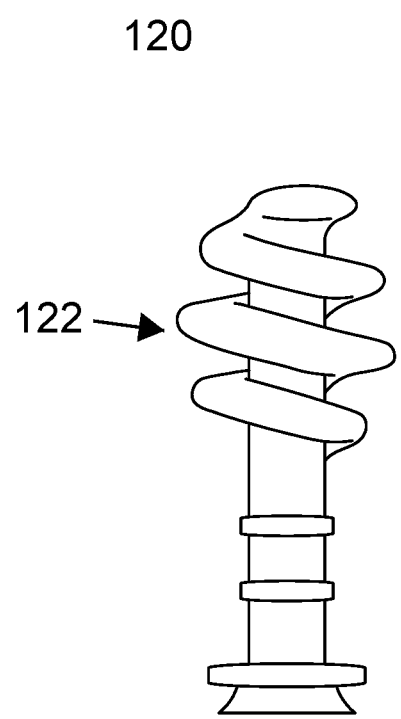
FIG. 16C shows the cleaning tip 120 having the spiral body 122 in oval shape arrangement according to specific embodiment(s) of the present invention.
Figure 22:
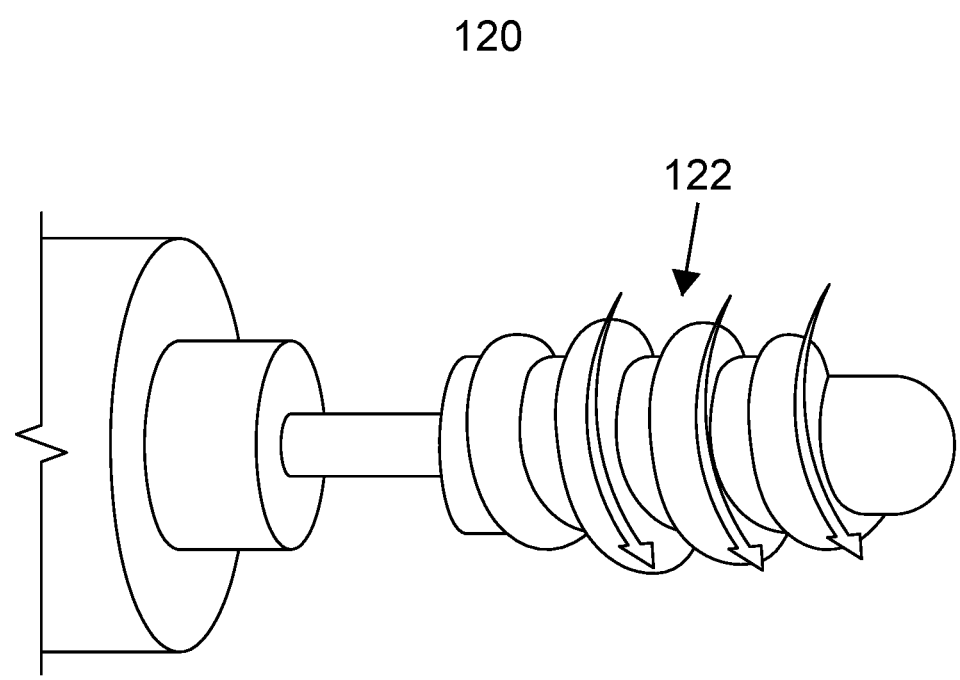
FIG. 22 shows the cleaning tip 120 having the spiral body 122 in the oval shape arrangement according to specific embodiment(s) of the present invention.

According to another embodiment of the invention, the spiral body 122 of the cleaning tip 120 includes an oval shape arrangement as shown in FIG. 9, FIG. 16C and FIG. 22. The oval shape arrangement may act as a stopper to prevent excessive insertion of the cleaning device I00 into ear or nose of a user.

According to another embodiment of the invention, the spiral body 122 of the cleaning tip 120 includes a cylindrical shape arrangement as shown in FIG. 16A and FIG. 16B.

Figure 2A:
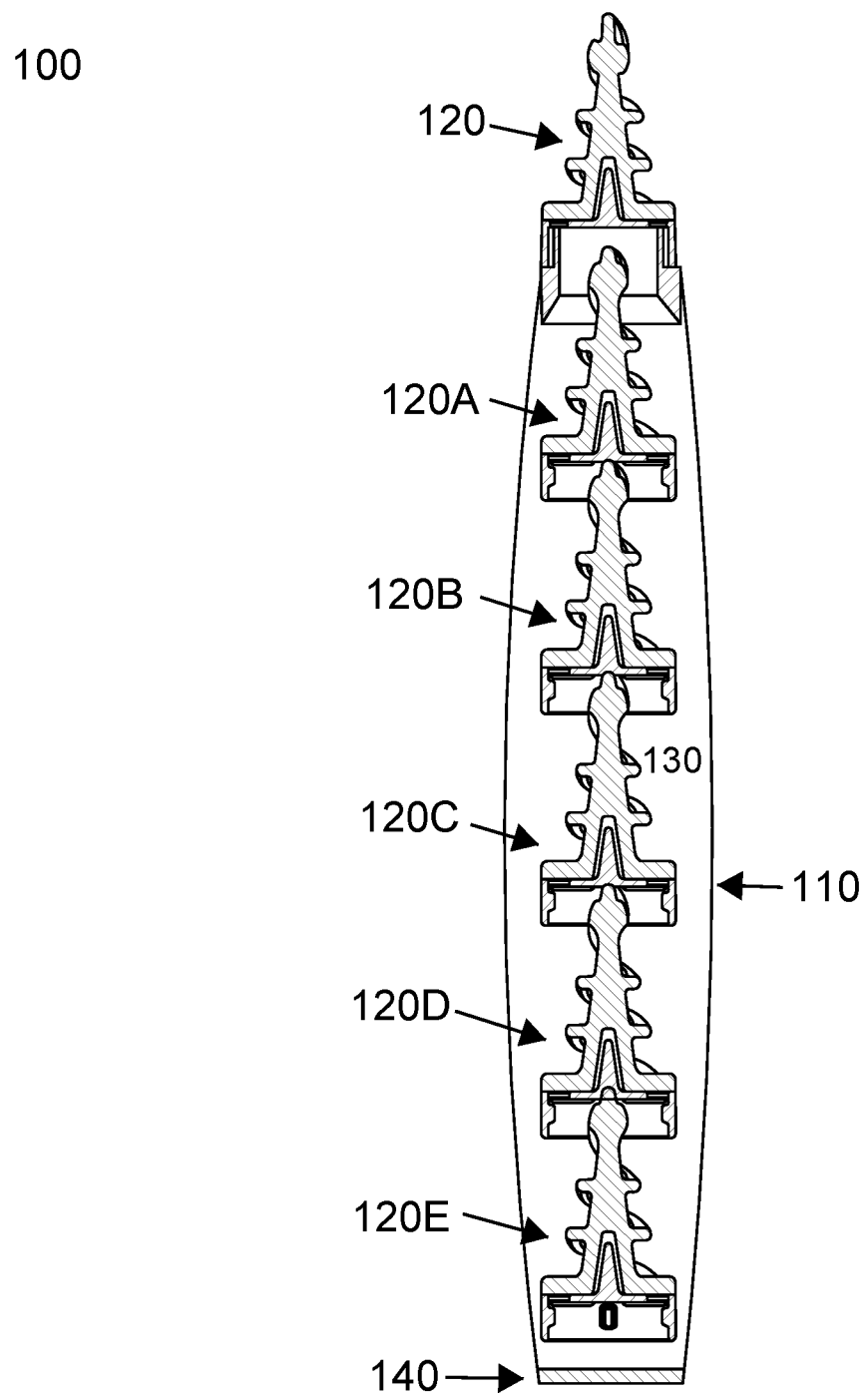

According to another embodiment of the invention, FIG. 2A shows a 3-D view of the ear and nose cleaning device 100 comprising of the handle 110, the cleaning tip 120 and at least one cartridge 130. The cartridge can be configured to store one or more cleaning tips 120A-120E. These tips may serve as additional/spare cleaning tips to replace the used cleaning tip. In one example, the handle comprises a hollow space that can act as the cartridge 130. In another example, the cartridge 130 can be a separate container inside the handle. In yet another example, the cartridge may be fixed or disposable. While using the ear and nose cleaning device, the user may not be aware of the number of spare cleaning tips stored inside the cartridge. The user may have to open the bottom cap and take out all the cleaning tips every time the user wants to find out the remaining number of spare tips in the cartridge. This becomes very inconvenient for the user.

Figure 2B:
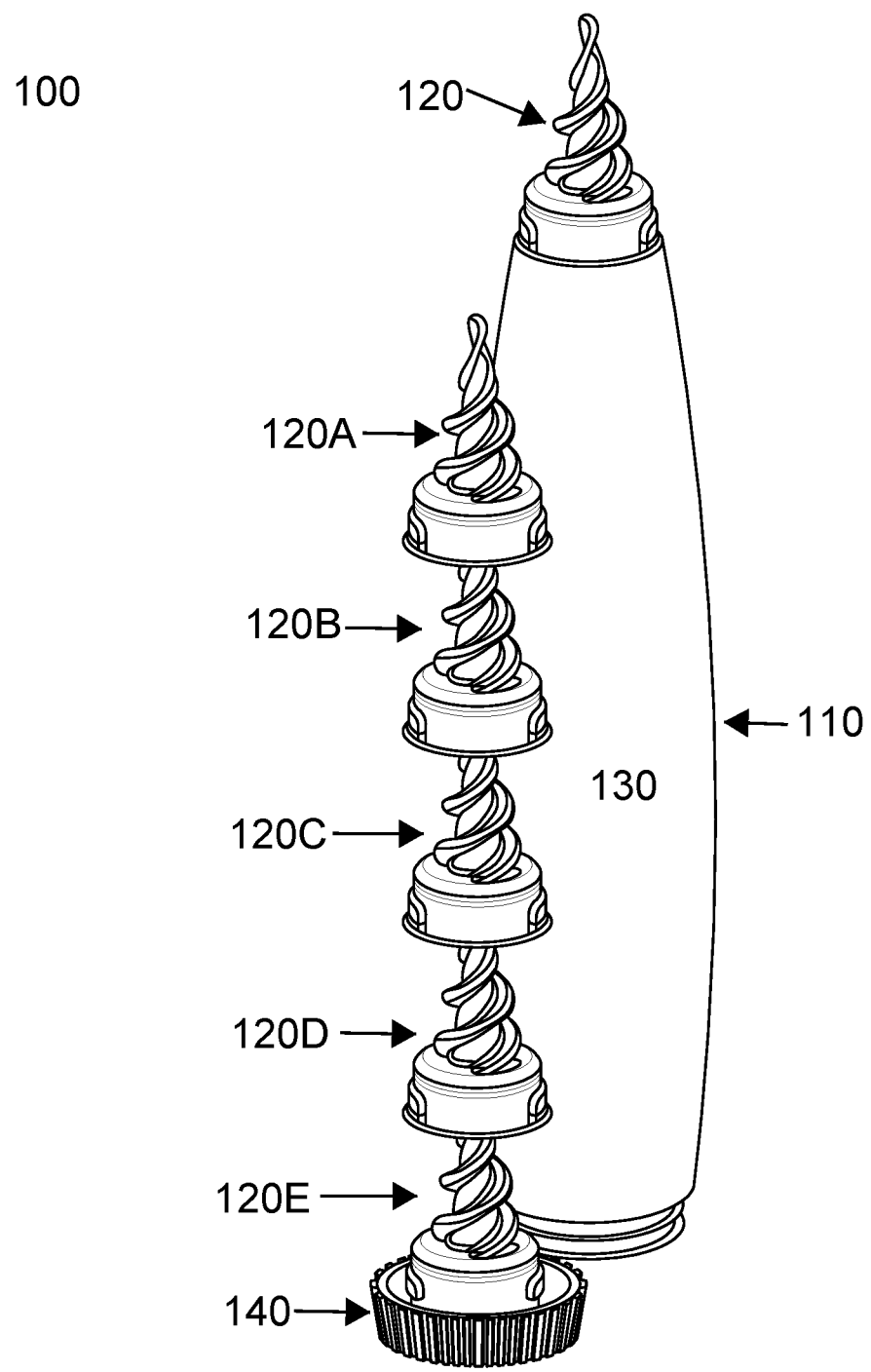

Further, if the hands of the user are soiled/dirty or wet, it may lead to contamination of the cleaning tips. The use of contaminated tips may cause infection in the ear and nose of the user. In order to overcome these drawbacks, one or more transparent windows 123 are provided on the body of the handle as shown in FIG. IA These transparent windows 123 help the user to see how many tips are stored or available inside the handle 110. FIG. 2B shows a 3-D view of the ear and nose cleaning device 100 comprising of the handle 110, the cleaning tip 120 and the at least one cartridge 130. In this figure, one or more cleaning tips 120A-120E are shown outside the handle 110 and the cartridge 130 for illustration purpose. In other words, FIG. 2B shows a 3-D view of the cleaning device 100 separated as 2 pieces, wherein one or more cleaning tips 120A-120E stored inside the cartridge 130 are shown outside the handle 110.

According to another embodiment of the invention, the at least one cartridge 130 can be configured to hold and dispense a fluid/composition that facilitates cleaning. In one example, the cleaning device 100 can be configured to dispense the fluid/composition from the cartridge 130 at a regulated pressure and/or dosage. In another example, mixing of two or more constituents from different cartridges can also take place in the cleaning device 100 to generate the fluid/composition that facilitates cleaning. Furthermore, the fluid/composition can comprise one or more cleaning agents/chemicals suitable for cleaning ear or nose of a user. For example, the cartridge 130 can be configured to store/hold and dispense/spray the fluid/composition suitable for cleaning ear, for example, washing, anti-bacterial treatment, medicating, drug-delivery, coating, drying (the ear or the wax or the dirt), dissolving wax, softening wax, soaking, flushing, rinsing, or the like According to another embodiment of the invention, the connection mechanism can be configured to form a releasable connection between the handle 110 and the cleaning tip 120. In one example, the releasable connection can be formed directly between the handle 110 and the cleaning tip 120 using their respective connection interfaces. In another example, the releasable connection can be formed indirectly via a connector between the handle 110 and the cleaning tip 120.

Figures 8A, 8B, 8C:
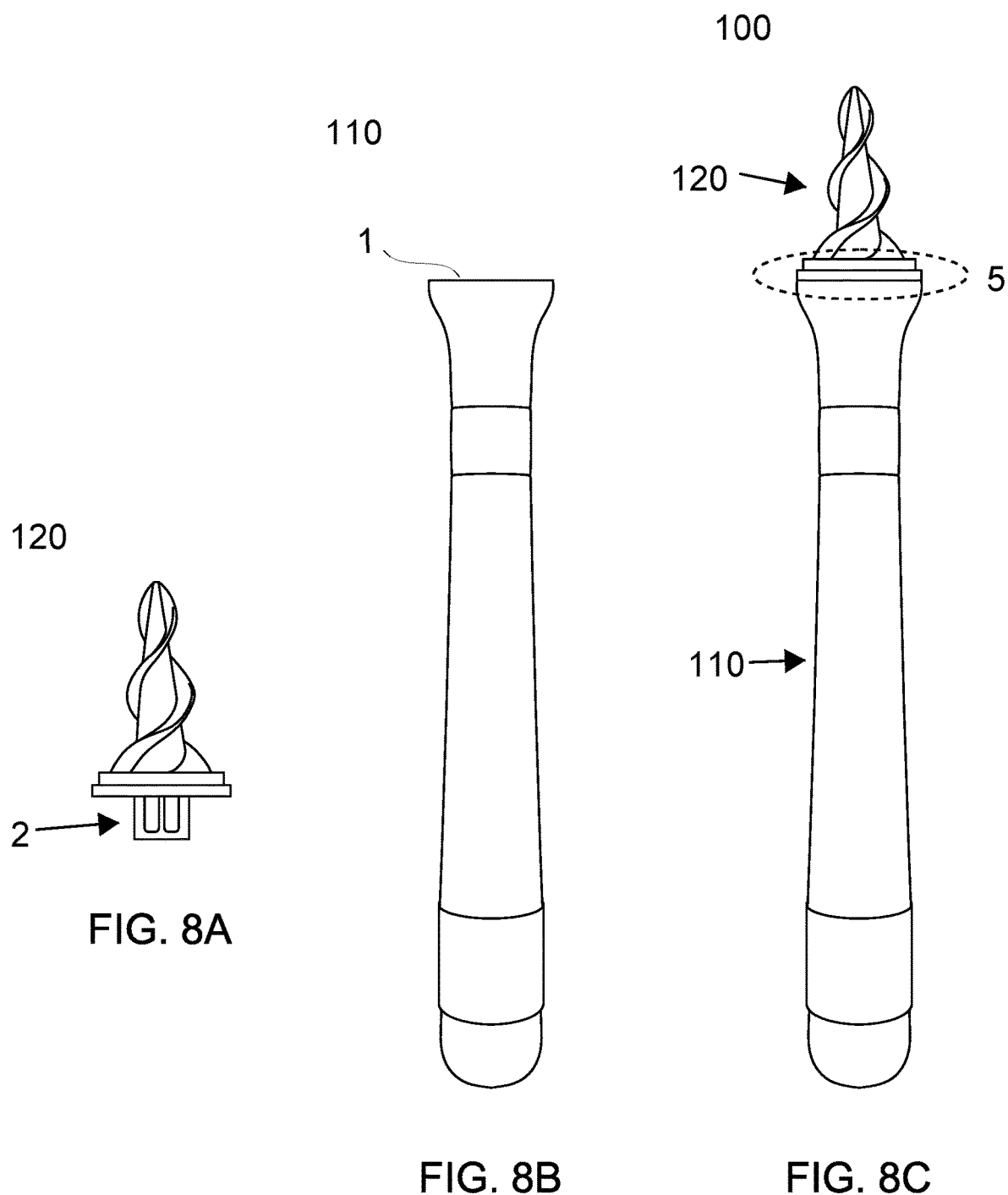
FIGS. 8A-8C show the connection mechanism to form the releasable connection according to specific embodiment(s) of the present invention.

According to another embodiment of the invention as shown in FIGS. 8A-8C, the connection mechanism may comprise a first connection interface 1 on the handle 110 and a second connection interface 2 on the cleaning tip 120 to form the releasable connection 5 between the handle 110 and the cleaning tip 120. FIG. 8C shows the cleaning device 100 having the handle 110 that can be coupled with the cleaning tip 120 without any connector(s). For example, the cleaning tip 120 and the handle 110 are shown in the disconnected form in FIG. 8A and FIG. 8B respectively. FIG. 8C shows the handle 110 and the cleaning tip 120 connected/coupled to each other without any connector in between.

Figure 3A:
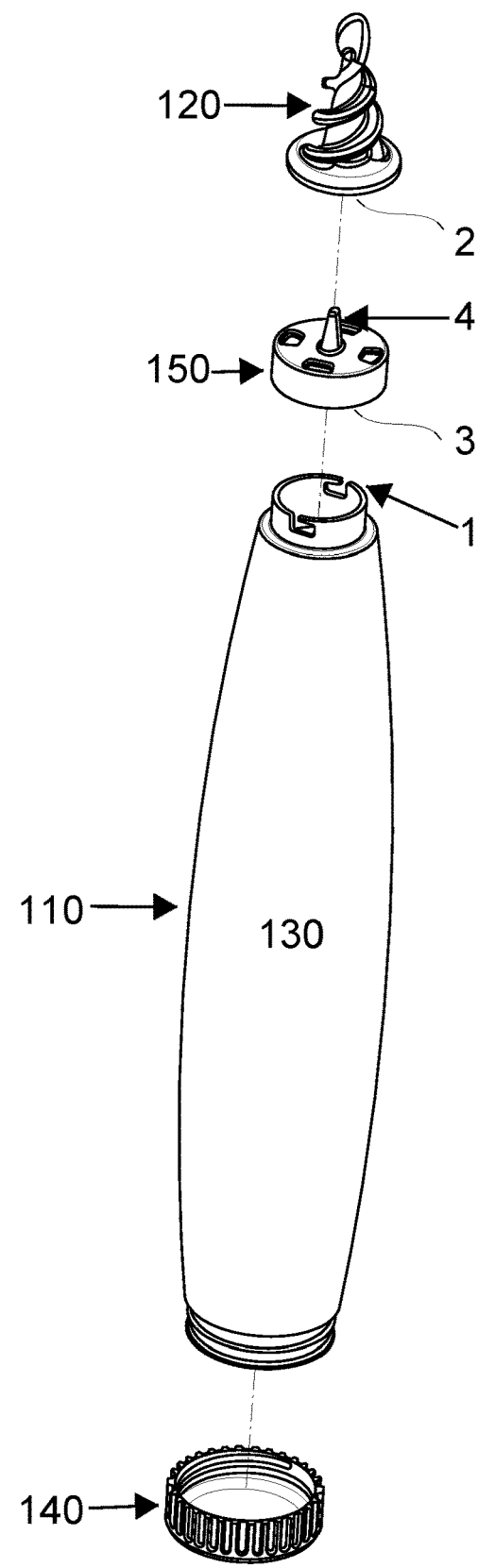

According to another embodiment of the invention, FIG. 3A shows a 3-D view of the ear and nose cleaning device 100 separated as 4 pieces. The cleaning device 100 may comprise of the handle 110, the cleaning tip 120, the connector 150 and the closure cap 140. Furthermore, the connection mechanism may comprise a first connection interface 1 on the handle 110 and a second connection interface 2 on the cleaning tip 120 to form the releasable connection 5 between the handle 110 and the cleaning tip 120. Additionally, the connection mechanism may comprise the connector 150 to form the releasable connection between the handle 110 and the cleaning tip 120. The connector 150 may further comprise of a third connection interface 3 configured to engage operatively with the handle 110 to form a first connection in a first direction; and a fourth connection interface 4 configured to engage operatively with the cleaning tip 120 to form a second connection in a second direction.

Figure 3B:
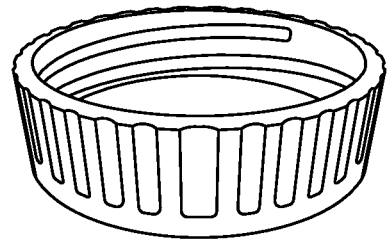
FIGS. 3B-3C show 3-D views of the closure cap 140 of the cleaning device 100 from different viewing angles according to specific embodiment(s) of the present invention.
Figure 3C:
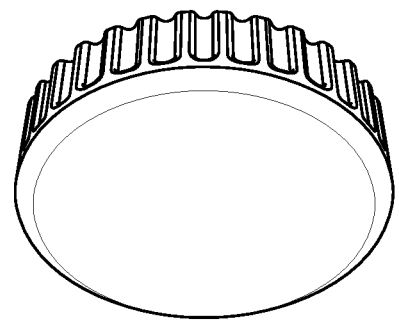

According to another embodiment of the invention, FIGS. 3B-3C show 3-D views of the closure cap 140 from different viewing angles.

According to another embodiment of the invention, at least one of the cleaning tips, the cartridge and the connection mechanism is disposable. In one example, the handle 110 of the cleaning device 100 can be configured with a suitable connection/locking mechanism to facilitate disposal of the used cleaning tip or cartridge, without the need of touching them, for cleanliness and better hygiene. Advantageously, this touch free replacement with a new cleaning or sterilized tip avoids contamination of the cleaning device 100 and/or the associated components.

Figures 4A, 4B, 4C, 4D:
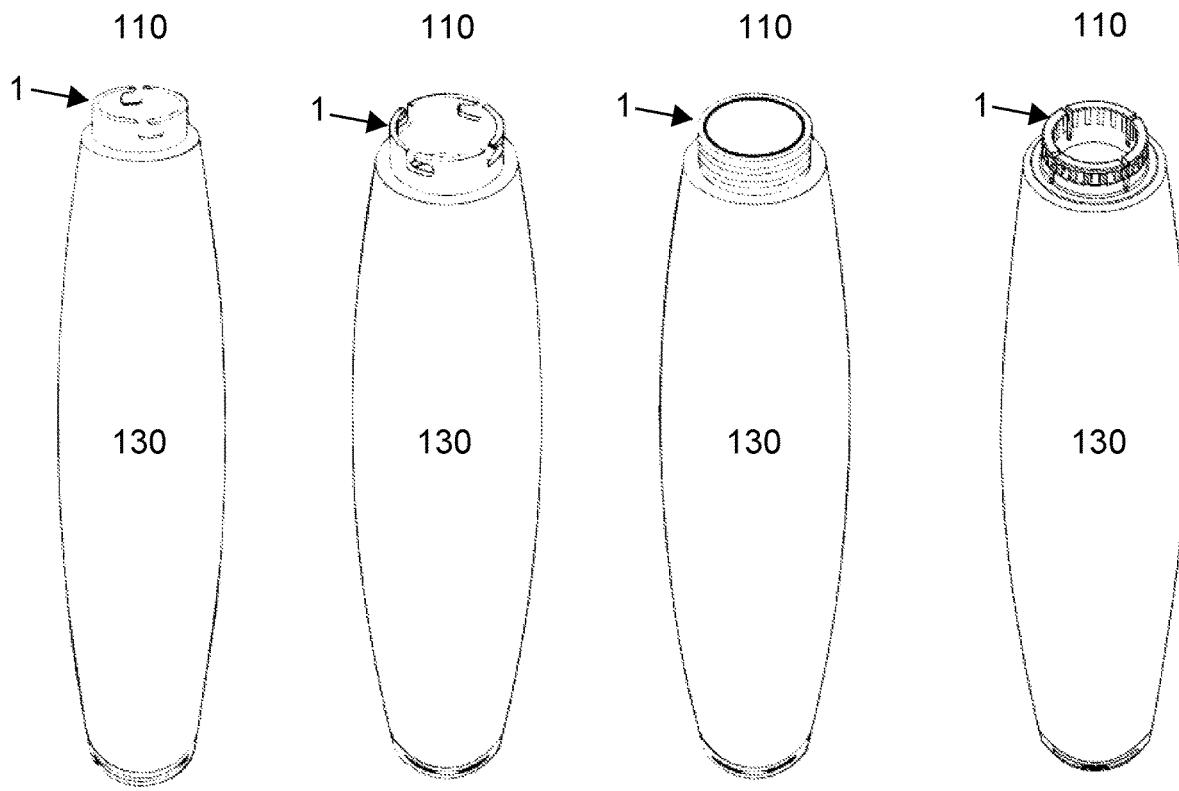
FIGS. 4A-4D show versions of the handle 110 having different types of connection interfaces according to specific embodiment(s) of the present invention.

According to another embodiment of the invention, FIGS. 4A-4C show versions of the handle 110 having different types of connection interfaces. FIG. 4A and FIG. 4B show the handle 110 having the first connection interface 1 that comprises of two and four slots respectively to couple with corresponding connection interface of the cleaning tip 120 and form the connection. FIG. 4C shows the handle 110 having the first connection interface 1 that comprises of screw threads to couple with corresponding connection interface of the cleaning tip 120 and form the connection.

Figures 5A, 5B, 5C:
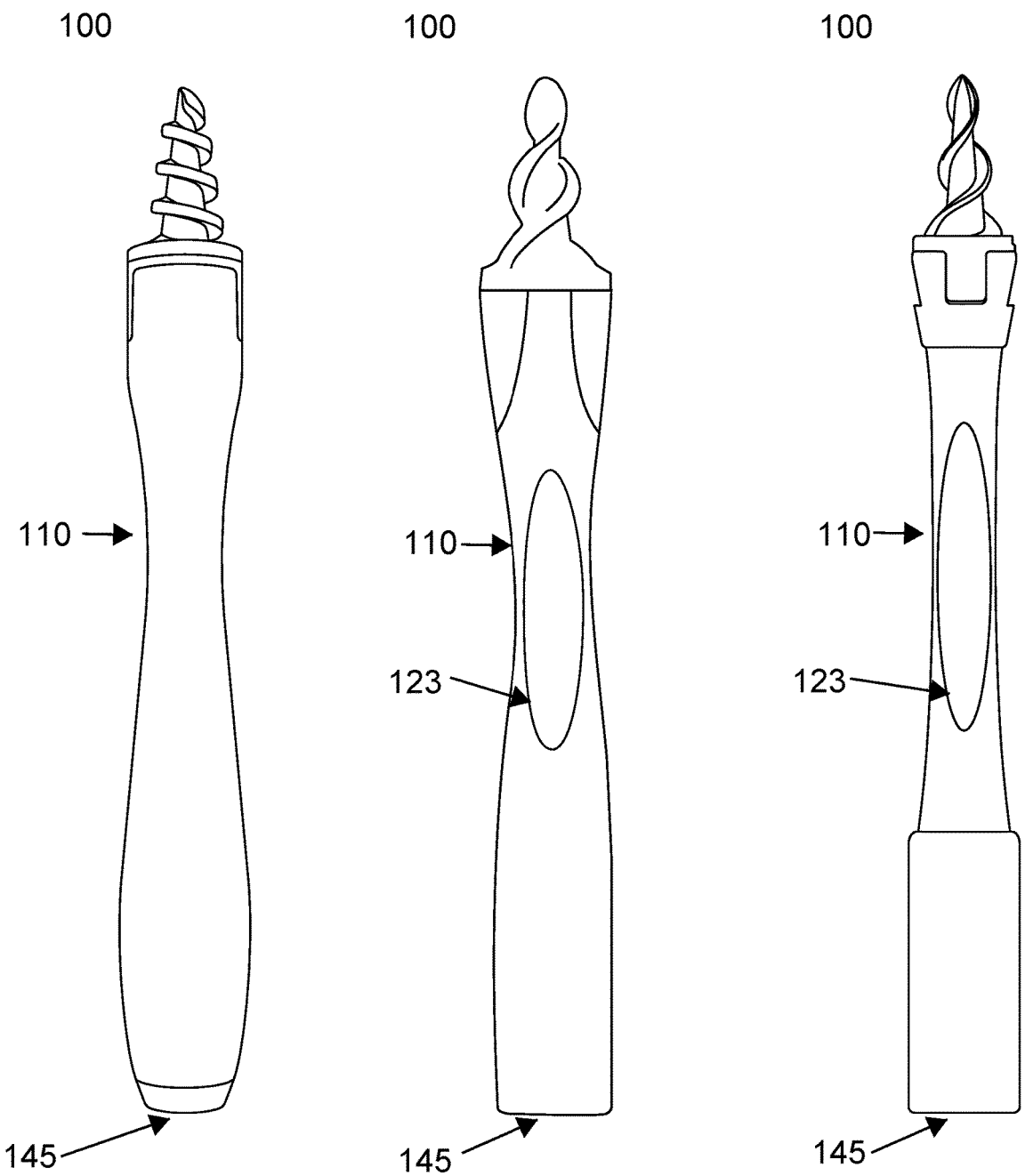
FIGS. 5A-5C show different versions of the cleaning device 100 having ergonomic design of the handle 110 and flat bottom design 145 according to specific embodiment(s) of the present invention.

According to another embodiment of the invention, FIGS. 5A-5C show different versions of the cleaning device 100 having ergonomic design of the handle 110 and flat bottom design 145.

Figure 6A:
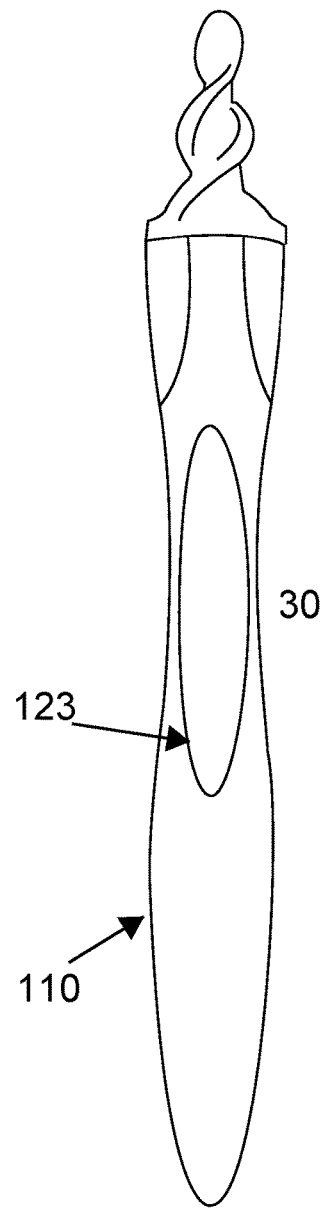
FIG. 6A-6C show different versions of the cleaning device 100 having a tapered style design/portion 30 of the handle 110 according to specific embodiment(s) of the present invention.
Figure 6B:
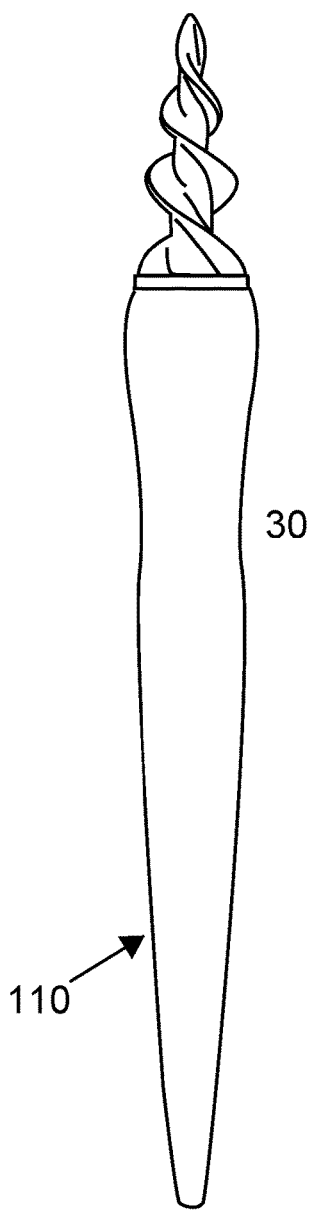
Figure 6C:
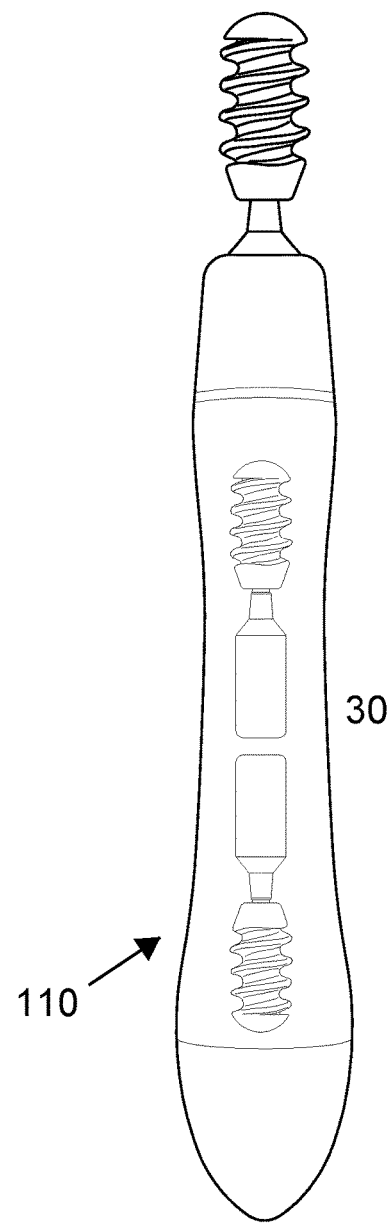
Figure 11:
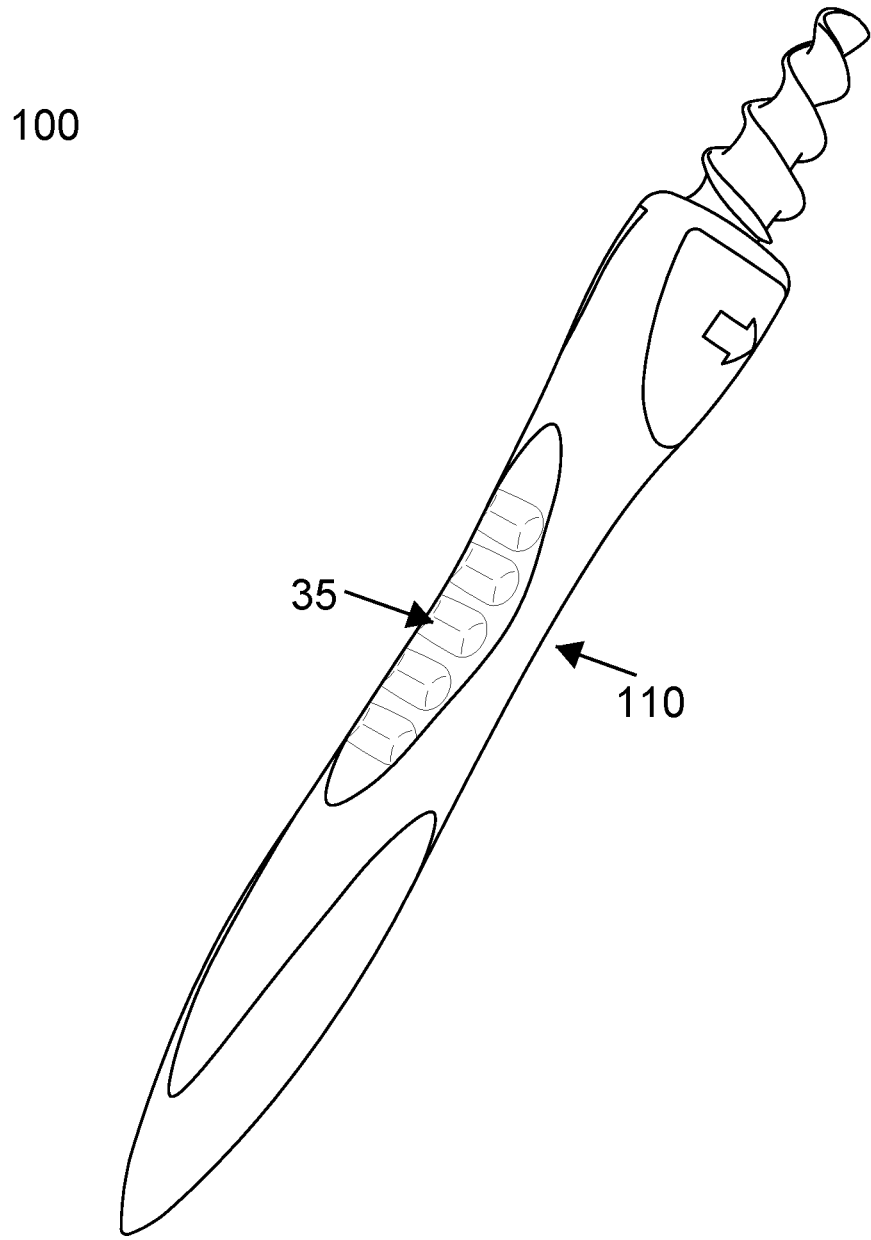
FIG. 11 shows a ribbed style design of the handle 110 having a ribbed portion 35 according to specific embodiment(s) of the present invention.
Figure 24A:
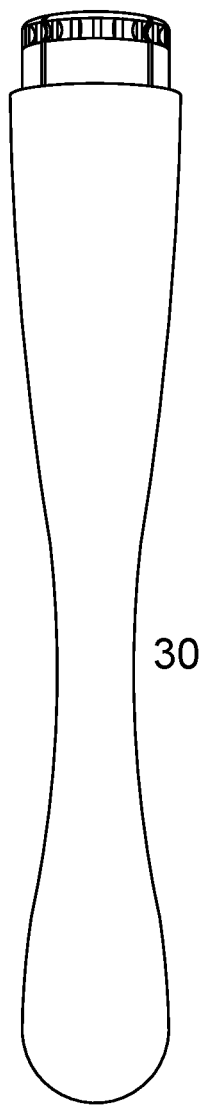
FIGS. 24A-24B show a side view and a perspective view respectively of the handle 110 with tapered waist 30 according to specific embodiment(s) of the present invention.
Figure 24B:
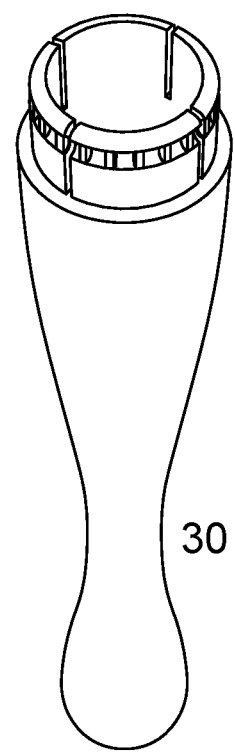

According to another embodiment of the invention, the handle 110 may include a tapered portion, a ribbed portion, or a combination thereof to provide better grip to a user. For example, FIGS. 6A-6C show different versions of the cleaning device 100 having a tapered style design/portion 30 of the handle 110. FIGS. 24A-24B shows a side view and a perspective view respectively of the handle 110 with tapered waist 30. FIGS. 25A-25B shows a side view and a perspective view of another version of the handle 110 with tapered waist 30. The difference between the versions of the handle 110 shown in FIGS. 24A-24B and FIGS. 25A-25B lies in the sizes/dimensions. In another example, FIG. 11 shows a ribbed style design of the handle 110 having a ribbed portion 35. Similarly, the handle 110 may comprise of a roughened surface portion/pattern. The purpose of these feature(s) is to provide a grip region which can assist in the ease of use of the cleaning device 100.

Figure 7:
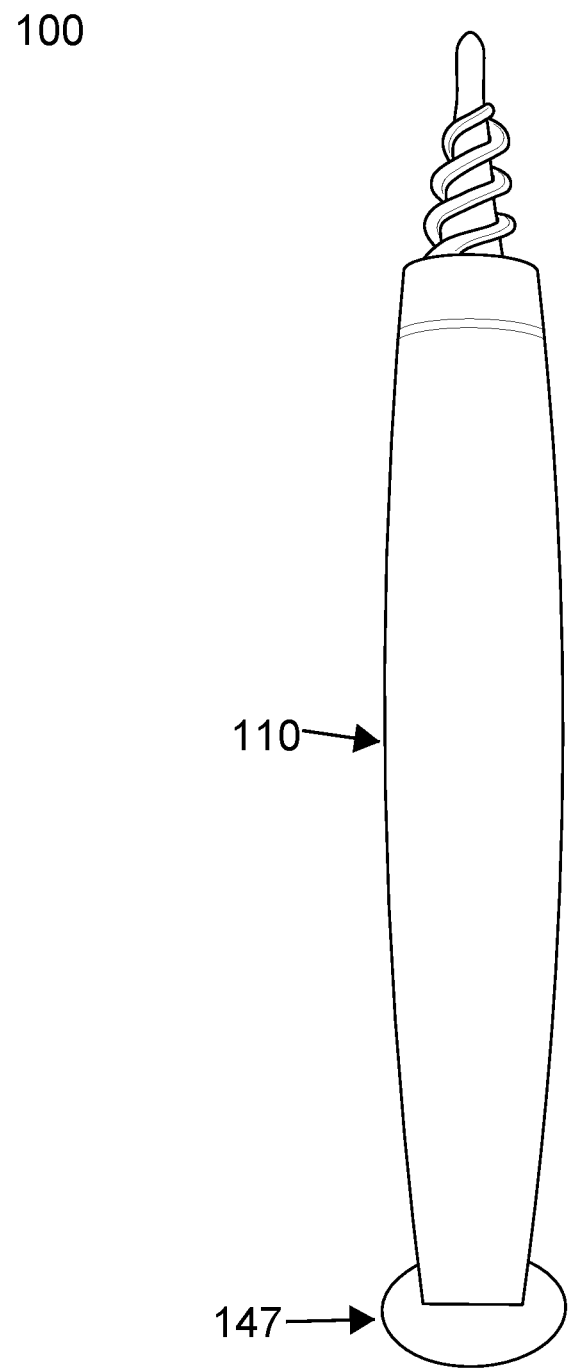
FIG. 7 shows the cleaning device 100 having a flat base 147 at bottom of the handle 110 according to specific embodiment(s) of the present invention.

According to another embodiment of the invention, FIG. 7 shows the cleaning device 100 having a flat base 147 at bottom of the handle 110 to stand on a surface. The flat base 147 can be attached to the handle 110. The flat base 147 can be round shape or any other shape suitable to provide a stable support for the cleaning device 100 to stand up on a surface.

According to another embodiment of the invention, FIG. 9 shows the cleaning device 100 having a stopper 20 to prevent excessive insertion of the cleaning device 100 and/or the cleaning tip 120 into ear canal or nose of a user. Therefore, the stopper plate 20 may safeguard ear drum from accidental perforation. In one example, the stopper 20 is adjustable and therefore its position can be adjusted according to a specific user. In another example, the stopper 20 can be located on the handle 110, the cleaning tip 120, or between the handle 110 and the cleaning tip 120. FIG. 9 also shows a button 110 configured to be pushed to actuate release of the cleaning tip 120 from the cleaning device 100.

Figure 10:
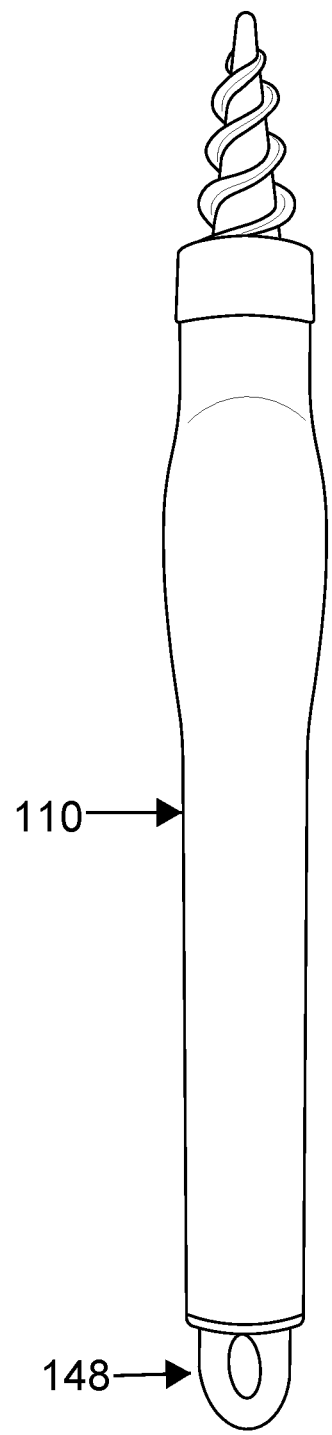
FIG. 10 shows the cleaning device 100 having a bottom hole/hook/hoop 148 according to specific embodiment(s) of the present invention.

According to another embodiment of the invention, FIG. 10 shows the cleaning device 100 having a bottom hole/hook/hoop 148 at bottom of the handle 110 for hanging.

Figure 12A:
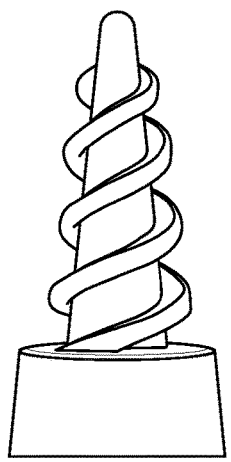
FIGS. 12A-12C show different versions/designs of the cleaning tip 120 with connection interface according to specific embodiment(s) of the present invention.
Figure 12B:
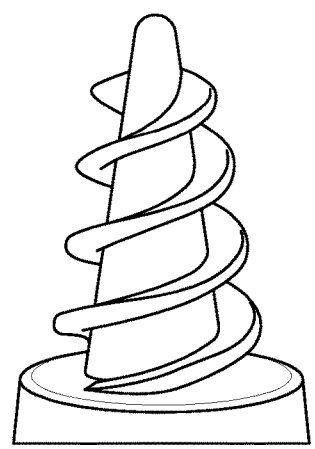
Figure 12C:
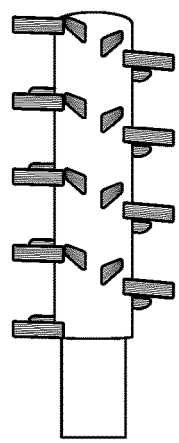

According to another embodiment of the invention, FIGS. 12A-12C show different versions/designs of the cleaning tip 120 with connection interface (that is, the second connection interface). FIG. 12A shows a cleaning tip 120A with a round connection interface as one piece.

Similarly, FIG. 12B shows a wider cleaning tip 120B with a round connection interface. FIG. 12C shows a cleaning tip 120C having a set of bristles arranged in spiral form. Furthermore, the connection interfaces of these cleaning tips may serve as the second connection interface 2 to form the releasable connection between the handle 110 and the cleaning tip 120 of the ear and/or nose cleaning device 100.

Figure 13A:
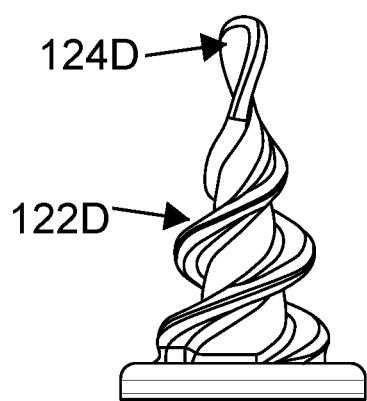
FIGS. 13A-13D show different versions of the cleaning tip 120 according to specific embodiment(s) of the present invention.
Figure 13B:
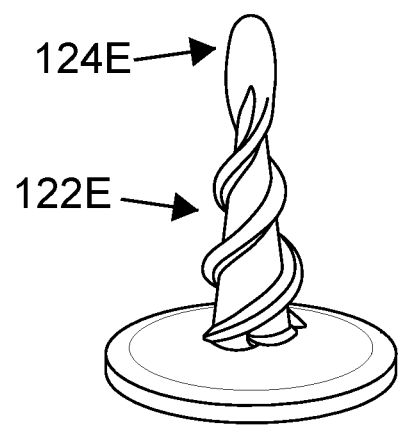
Figure 13C:
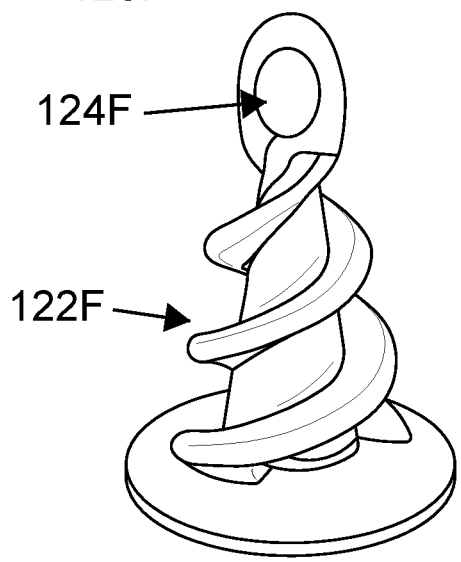
Figure 13D:
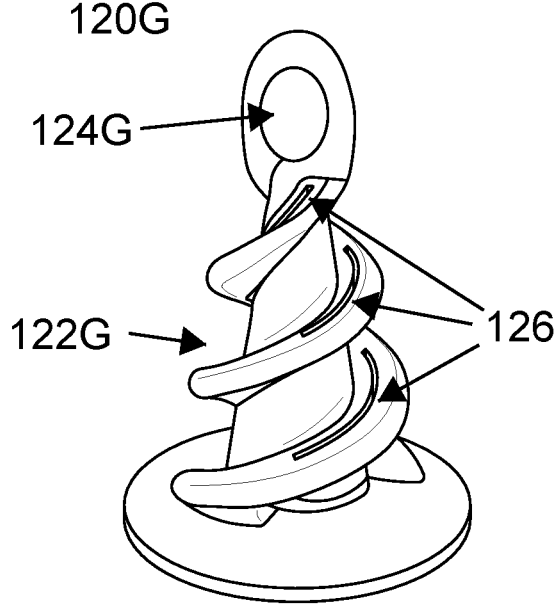
Figure 13E:
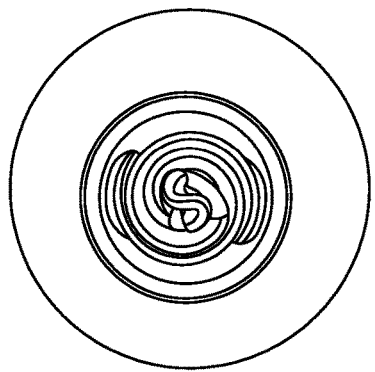
FIG.13E and FIG. 13F show top view of the cleaning tips shown in FIG. 13A and FIG. 13B respectively.
Figure 13F:
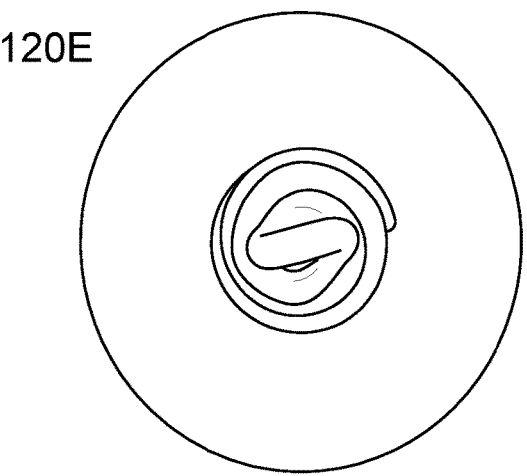

According to another embodiment of the invention, FIGS. 13A-13D shows different versions of the cleaning tip 120. The different versions of the cleaning tip 120 have different sizes/dimensions/shapes so that a cleaning tip is used which is suitable for a particular size or age of child/adult. FIG. 13A shows a cleaning tip 120D with the curved shape feature 124D (for example, spoon) and/or the spiral body 122D suitable for an adult. FIG. 13B shows a cleaning tip 120E with the curved shape feature 124E and/or the spiral body 122E suitable for a child. FIG. 13C shows a cleaning tip 120F with a hollow spoon shape feature 124F and/or the spiral body 122F. FIG. 13D shows a cleaning tip 120G with a hollow spoon shape feature 124G, the spiral body 122G having a hollow space 126 within the fms spiraling up. Furthermore, the cleaning tip with hollow space can be incorporated in any of the cleaning tip designs. FIG.13E and FIG. 13F show top view of the cleaning tips 120D and 120E shown in FIG. 13A and FIG. 13B respectively.

Figures 14A, 14B:
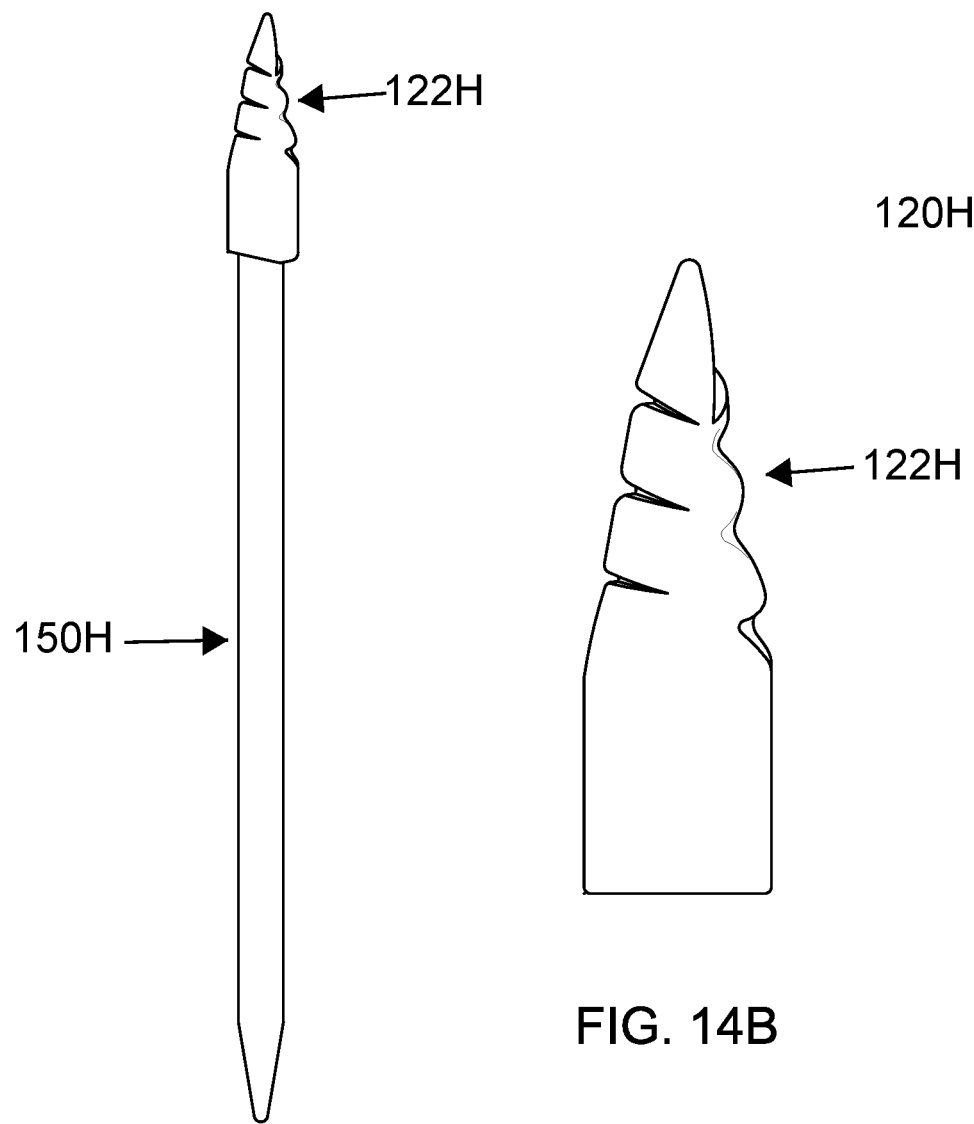
FIG. 14A and FIG. 14B show a cleaning tip 120H having a spiral body 122H in a conical arrangement according to specific embodiment(s) of the present invention.

According to another embodiment of the invention, FIG. 14A and FIG. 14B show a cleaning tip 120H having a spiral body 122H in a conical arrangement. The cleaning tip 120H can be attached/detached to/from a connector 150H. Therefore, the cleaning tip 120H is replaceable. The connector 150H can be a cylindrical shaft/stick as shown in FIG. 14A. The connector 150H can be configured to couple with the handle 120 on the one side and the cleaning tip 120H on the other side to form the releasable connection.

Figure 15A:
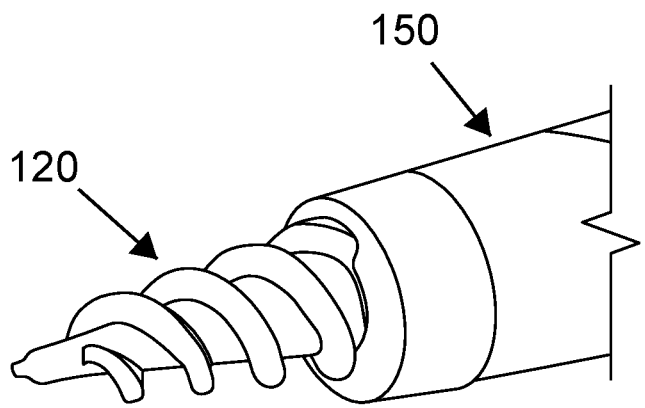
FIG. 15A shows a spiral cleaning tip 120 attached/coupled with the connector 150 according to specific embodiment(s) of the present invention.
Figure 15B:
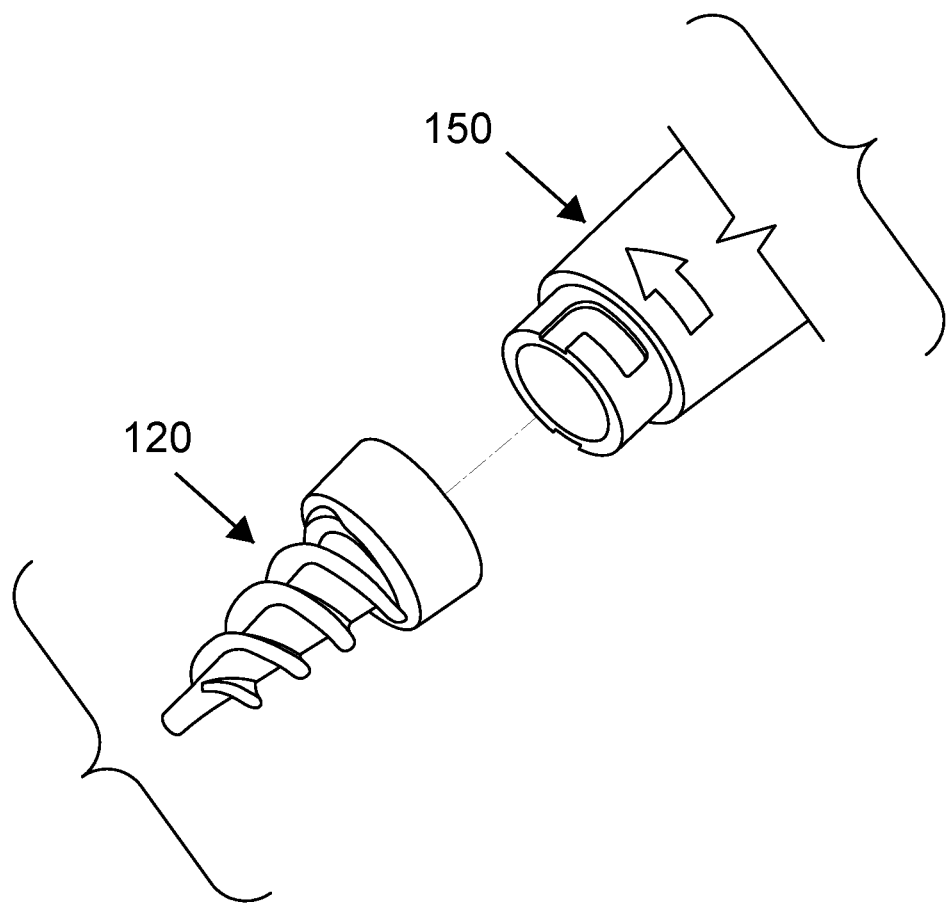
FIG. 15B shows a twist connection of the cleaning tip 120 and the round connector 150 according to specific embodiment(s) of the present invention.

According to another embodiment of the invention, FIG. ISA shows a spiral cleaning tip 120 attached/coupled with the connector 150. In one example, multiple connectors and/or cleaning tips of different colors or sizes can be provided so that different family members may use their respective connectors and/or cleaning tips with different color or size. In another embodiment FIG. 15B shows a twist connection of the cleaning tip 120 and the round connector 150.

Figure 17A:
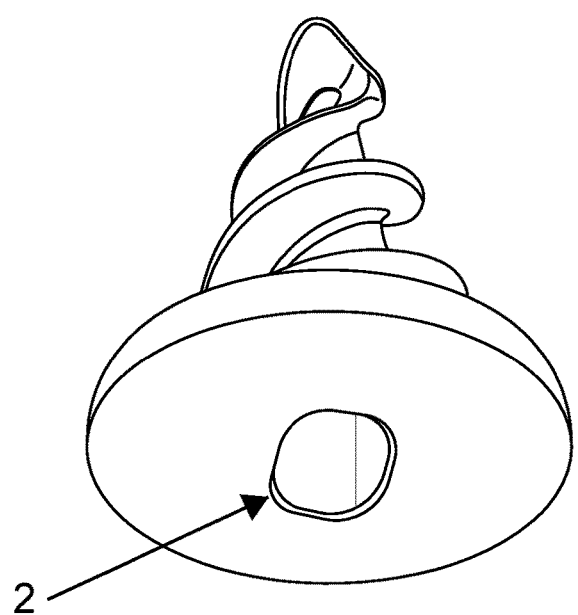
FIG. 17A shows the cleaning tip 120 with a connection interface suitable for rectangular connector/shaft according to specific embodiment(s) of the present invention.

According to another embodiment of the invention, FIG. 17A shows the cleaning tip 120 with a connection interface (the second connection interface 2) suitable for rectangular connector/shaft.

Figure 17B:
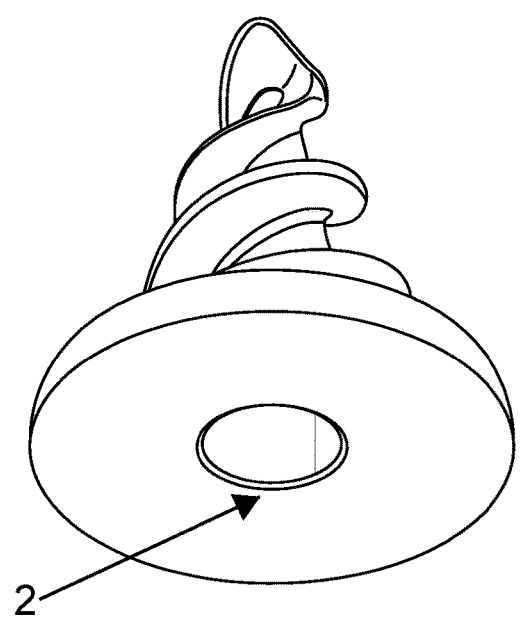
FIG. 17B shows the cleaning tip 120 with a connection interface suitable for round shaped connector/shaft according to specific embodiment(s) of the present invention.

In another embodiment, FIG. 17B shows the cleaning tip 120 with a connection interface (the second connection interface 2) suitable for round shaped connector/shaft.

Figure 18:
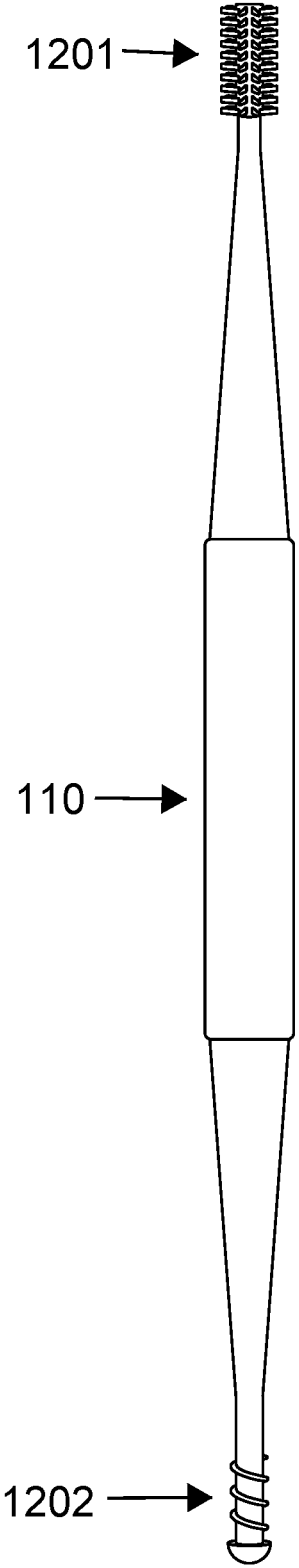
FIG. 18 shows the cleaning device 100 having the handle 110 connected/coupled to two different cleaning tips on its sides according to specific embodiment(s) of the present invention.
Figures 19A, 19B:
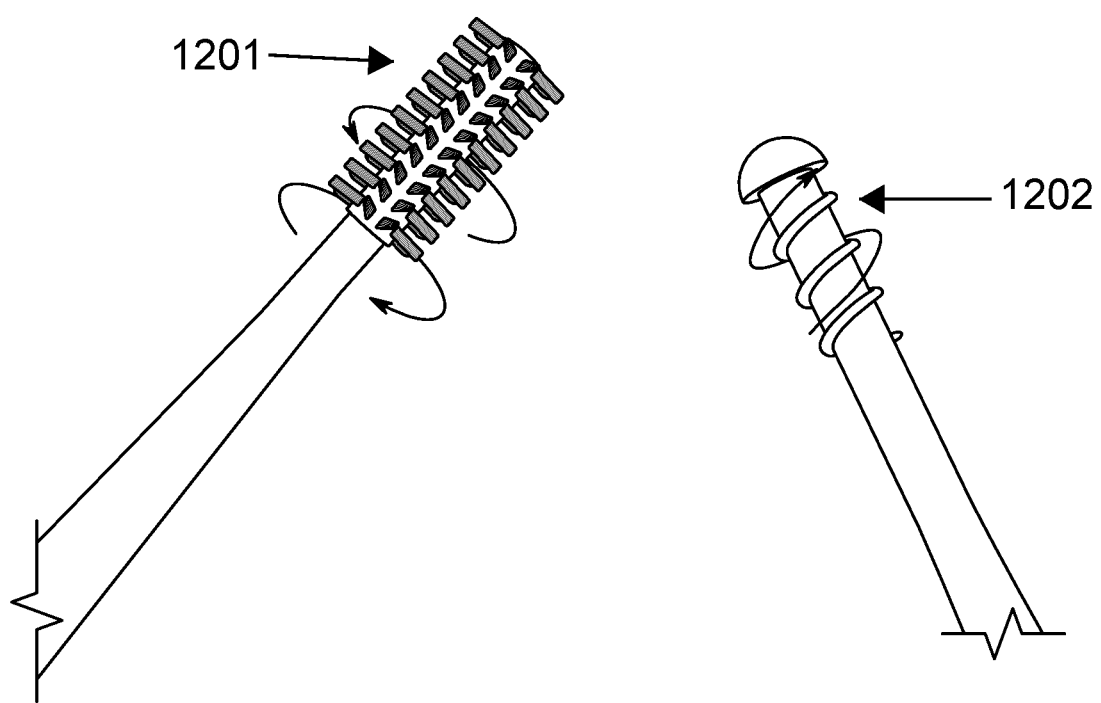
FIG. 19A and FIG. 19B show closeup views of the cleaning tips disclosed in FIG. 18.
Figure 20:
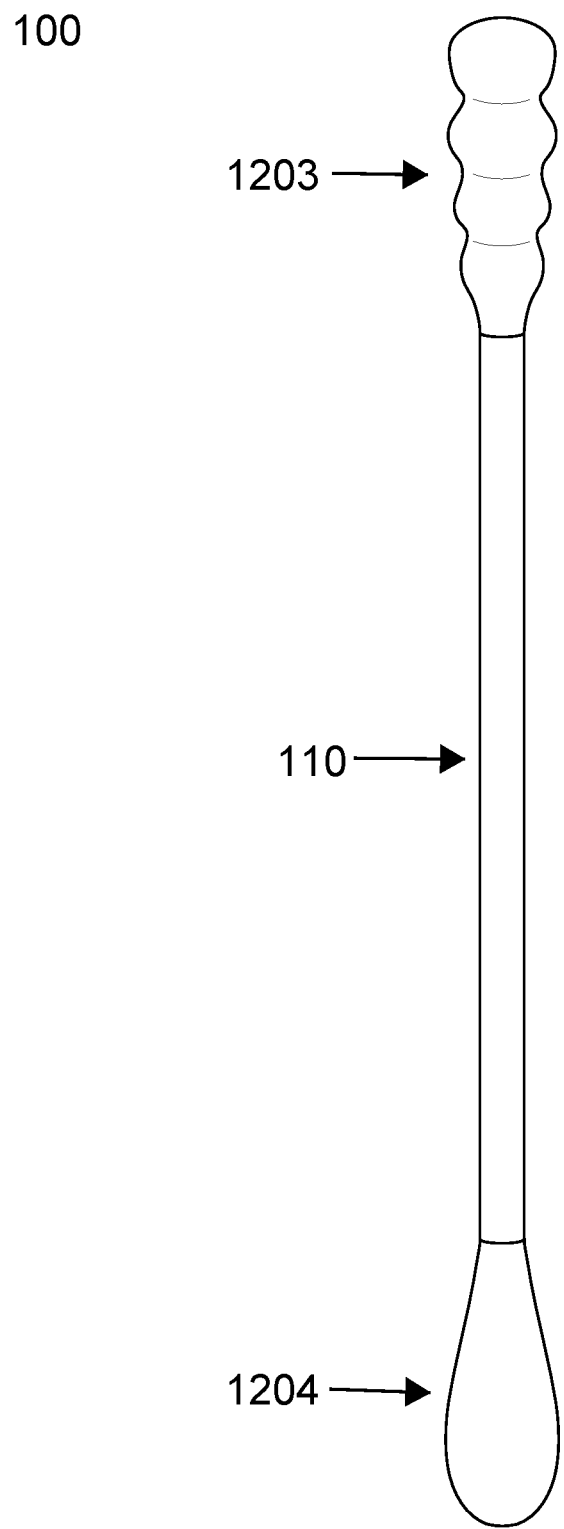
FIG. 20 shows the cleaning device 100 having one end of the handle 110 connected/coupled to the cleaning tip 1204 that comprises the curved shape feature, and other end of the handle 110 connected/coupled to the cleaning tip 1203 that comprises the spiral body.
Figure 21:
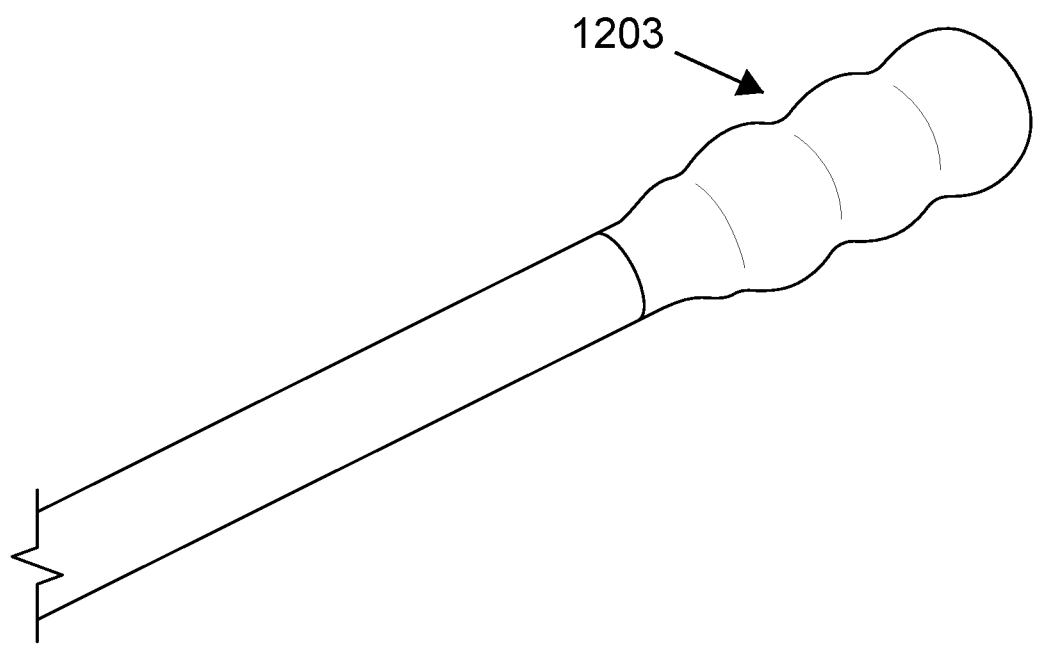
FIG. 21 shows a closeup of the cleaning tip 1203 having the spiral body in oval shape arrangement, as disclosed in FIG. 20.

According to another embodiment of the invention, FIG. 18 shows the cleaning device 100 having the handle 110 connected/coupled to two different cleaning tips on its sides. The handle 110 can be connected/coupled to the cleaning tip 1201 having the set of bristles on its one side/end and the handle 110 can be connected/coupled to the cleaning tip 1202 having the spiral body on its other side/end. Furthermore, the set of bristles can be arranged in spiral form as shown and described in FIG. 12C earlier. FIG. 19A and FIG. 19B show closeup views of the cleaning tips disclosed in FIG. 18. Specifically, FIG. 19A shows closeup of the cleaning tip 1201 having the set of bristles, and FIG. 19B shows closeup of the cleaning tip 1202 having the spiral body According to another embodiment of the invention, one end of the handle 110 can be coupled to the cleaning tip having the spiral body and/or the at least one curved shape feature, and other end of the handle can be coupled to the cleaning tip having the set of bristles and/or the at least one curved shape feature. For example, FIG. 20 shows the cleaning device 100, wherein one end of the handle 110 can be connected/coupled to the cleaning tip 1204 having the curved shape feature and other end of the handle 110 can be connected/coupled to the cleaning tip 1203 having the spiral body. Furthermore, the spiral body of the cleaning tip 1203 may include the oval arrangement disclosed earlier. FIG. 21 shows a closeup of the cleaning tip 1203 having the spiral body in oval shape arrangement, as disclosed in FIG. 20.

Figure 23A:
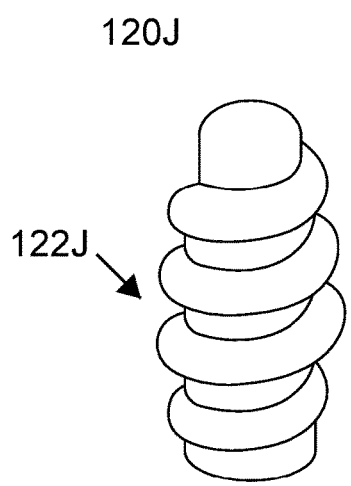
FIGS. 23A-23C show different versions of the cleaning tip(s) 120 having the spiral body in the oval shape arrangement according to specific embodiment(s) of the present invention.
Figure 23B:
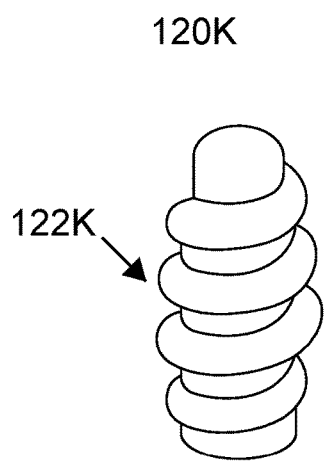
Figure 23C:
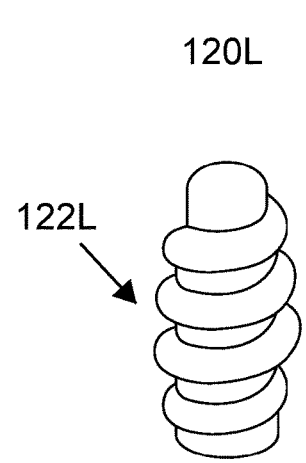

According to another embodiment of the invention, FIG. 22 shows the cleaning tip 120 having the spiral body 122 in the oval shape arrangement. FIGS. 23A-23C show different versions of the cleaning tip(s) 120 having the spiral body in the oval shape arrangement. The three versions of the cleaning tips 120J, 120K and 120L (having the spiral bodies 122J, 122K and 122L respectively) differ in sizes so as to make them suitable for different individuals and/or age groups.

Figure 26A:
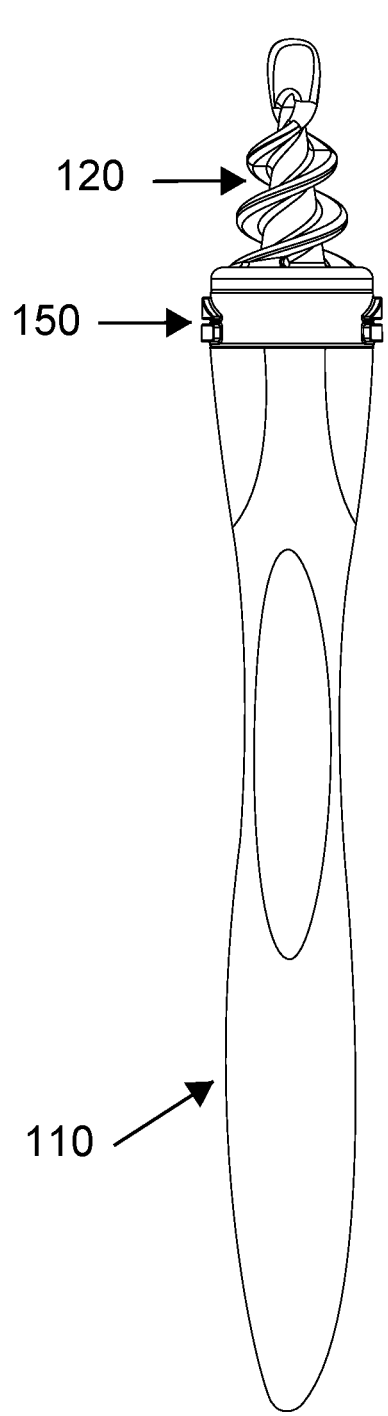
FIG. 26A shows an ear and nose cleaning device 100 with a connector 150 according to specific embodiment(s) of the present invention.
Figure 26B:
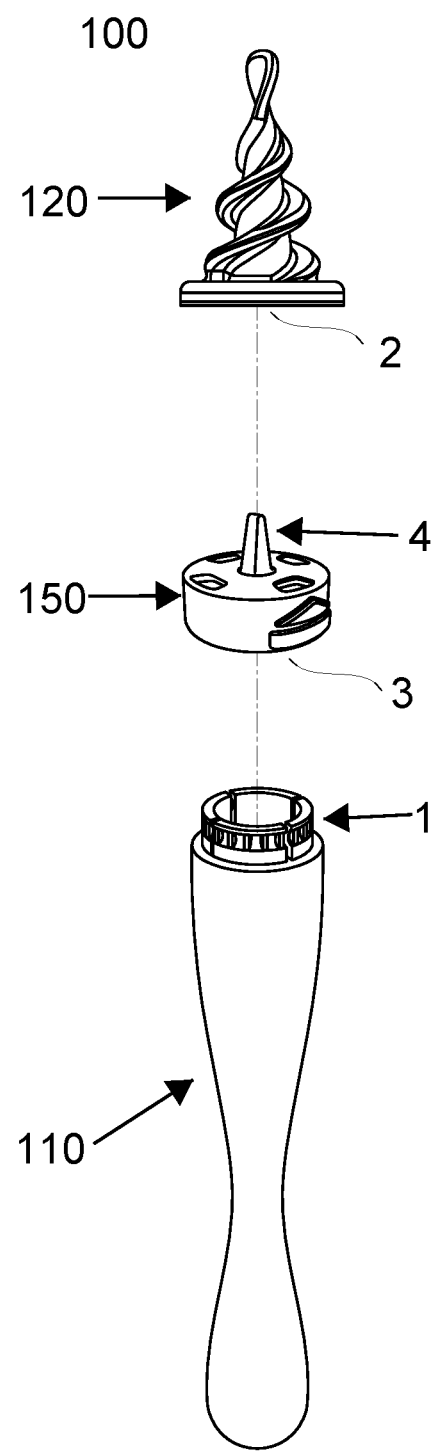
FIG. 26B shows a 3-D view of the ear and nose cleaning device 100, separated as 3 pieces, according to specific embodiment(s) of the present invention.

According to another embodiment of the invention, FIG. 26A shows an ear and nose cleaning device 100 comprising the handle 110, a connector 150, and the cleaning tip 120. FIG. 26B shows a 3-D view of the ear and nose cleaning device 100 separated as 3 pieces. The cleaning device 100 may comprise of the handle 110, the cleaning tip 120 and the connector 150. Furthermore, the connection mechanism may comprise the first connection interface 1 on the handle 110 and the second connection interface 2 on the cleaning tip 120 to form the releasable connection between the handle 110 and the cleaning tip 120. Additionally, the connection mechanism may comprise the connector 150 to form the releasable connection between the handle 110 and the cleaning tip 120. The connector 150 may further comprise of the third connection interface 3 configured to engage operatively with the handle 110 to form the first connection in the first direction; and the fourth connection interface 4 configured to engage operatively with the cleaning tip 120 to form the second connection in the second direction.

Figure 27A:
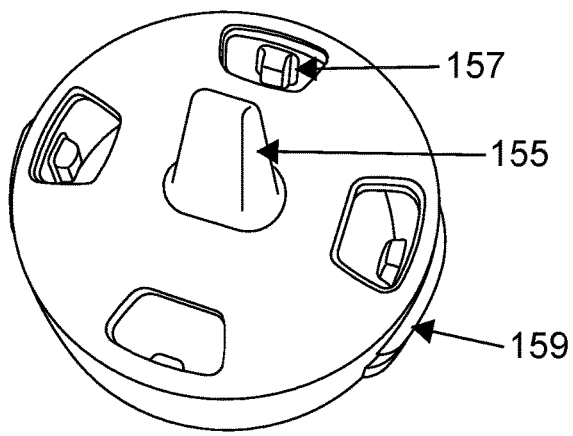
FIG. 27A and FIG. 27B show different views of the connector 150 having a rectangular shaft 155, a plurality of nipples 157 and an ejector 159 according to specific embodiment(s) of the present invention.
Figure 27B:
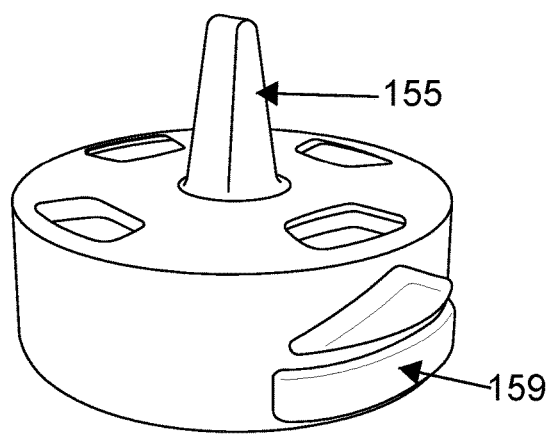
Figure 28:
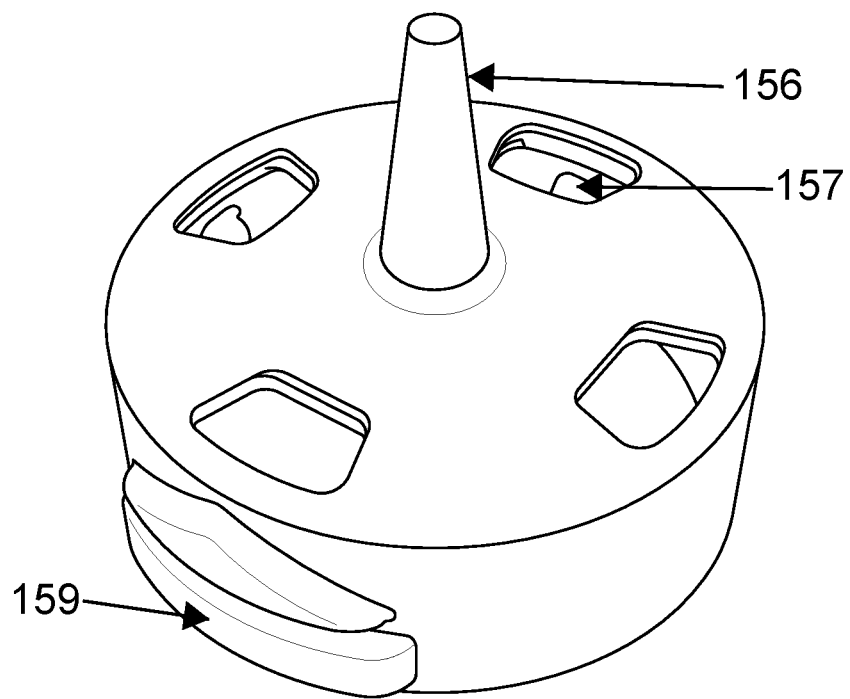
FIG. 28 shows a 3-D view of another version of the connector 150 having a circular shaft 156, the plurality of nipples 157 and the ejector 159 according to specific embodiment(s) of the present invention.

According to another embodiment of the invention, FIG. 27A and FIG. 27B show different views of the connector 150 having a rectangular shaft 155, a plurality of nipples 157 (for example, 4 nipples) and an ejector 159. In one example, the rectangular shaft 155 and the plurality of nipples 157 can together function as the connection interface 4 to engage with the cleaning tip 120 and form the connection. The ejector 159 can function as a mechanism (for example, a pushing mechanism) to eject the used cleaning tip upon disengagement. In another embodiment, FIG. 28 shows a 3-D view of another version of the connector 150 having a circular shaft 156, the plurality of nipples 157 and the ejector 159.

According to another embodiment of the invention, one or more connection interfaces described in the specification can be designed in various shapes and/or sizes so as to form a reliable and/or the releasable connection. For example, the connection interface can comprise of rib(s), tub(s), pin(s), bar(s), brush(es), comb(s), shaft(s) or protruding member(s), for the cleaning tip, the handle and/or the connector to lock into each other, with corresponding/matching gap(s), slit(s), opening(s), cut(s) or aperture(s) on the other side to engage with the other side, to lock in and attach with each other as one unit. In one example, the locking can be done by pushing these two parts toward each other, to snap into a locked position. To release, the locked parts can be operated or pushed by fingers of a user so as to pull apart the parts simultaneously and get the parts separated from each other. In other example, the connection(s) between the handle 110, the connector 150 and/or the cleaning tip 120 can be a threaded connection, a snug fit connection, a locking/keying connection, or the like. Basically, these types of connections (for example, locking/keying connection) ensure one connection interface to engage with corresponding/complementary arrangement on the other connection interface so as to form a reliable and/or releasable connection.

Moreover, the connection interface(s) can be also configured and/or shaped to limit the connection capability of the cleaning device 100 in relation to compatible connector(s) 150, compatible cartridges 130 and/or compatible cleaning tip(s) 120. This compatibility feature may ensure safe and/or efficient operation of the cleaning device 100. Advantageously, this feature may also ensure proper working of the cleaning device 100 with genuine and/or compatible parts.

According to another embodiment of the invention, the cleaning tip 120 includes a flexible and/or soft material. For example, at least a portion of the cleaning tip 120 can be made of open cell foam, moist absorbent, regular foam, sponge, cotton, cloth, soft tissue, towel, Q-tip material, wool, silk, nylon, acrylic, petroleum-based material, synthetic material, porous material for absorbing moisture and liquid, dry fabric, filter material, coarse material, bumpy surface material, or the like. Furthermore, the cleaning tip 120 having a soft or elastic/flexible material can be required for efficient and safe operation of the cleaning device 100.

According to another embodiment of the invention, the cleaning tip 120 for use in the ear and nose cleaning device 100 is also disclosed. The cleaning tip 120 comprises the spiral body 122 that includes one of the oval shape arrangements and the cylindrical shape arrangement, the at least one curved shape feature 124, or a combination thereof. The cleaning tip 120 is configured to couple with the handle 110 of the ear and nose cleaning device 100 using the connection mechanism disclosed earlier.

Figure 29:
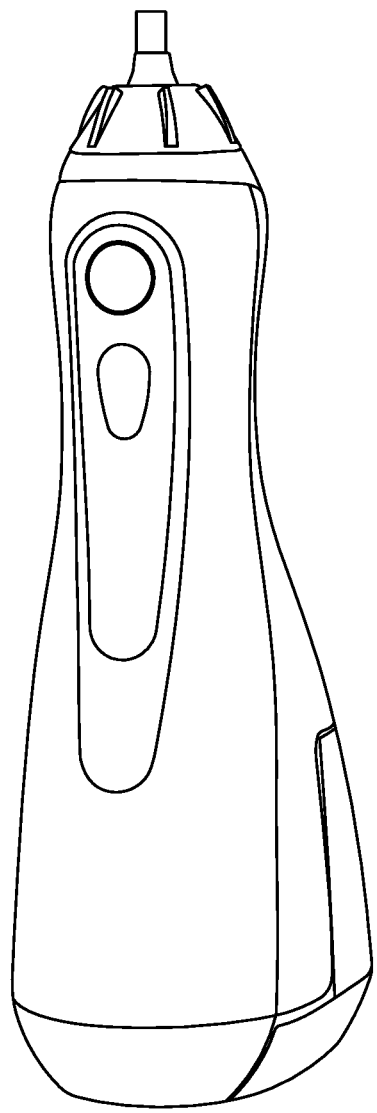
FIG. 29, FIGS. 30A-30B, and FIG. 31 illustrate electronic versions of the handle1100 of the ear and/or nose cleaning device according to specific embodiment(s) of the present invention.
Figure 30A:
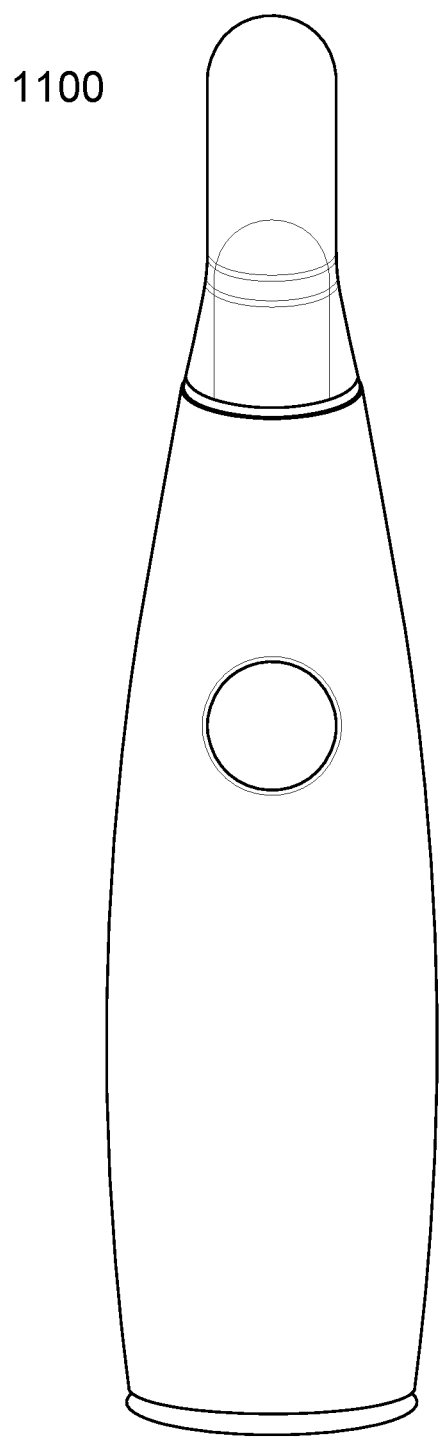
Figure 30B:
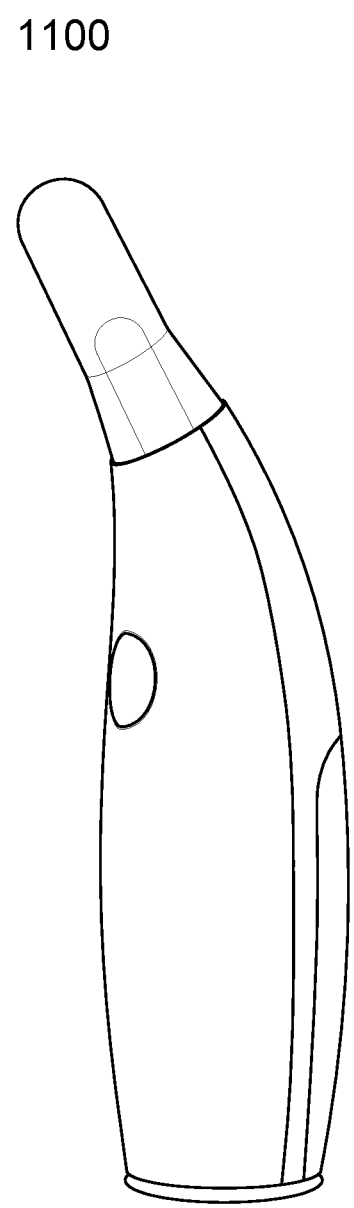

According to another embodiment of the invention, FIG. 29 shows an electronic version of the handle 1100 of the ear and/or nose cleaning device. The handle 1100 can be configured to operate electronically to dispense the fluid/composition from the at least one cartridge and facilitate cleaning. The handle 1100 can comprise a power button to switch on/off the cleaning device and a light indicator to indicate the working mode, status or functionality of the device. The handle 1100 can also have a flashlight or an LED light at a suitable position to provide illumination at the time/point of use. The handle 1100 can comprise further of additional components such as, but not limited to, microprocessor/microcontroller, battery, pump, vacuuming unit, valve mechanism, mixing chamber, etc. for electronic and/or automated functioning of the cleaning device in a controlled manner. In one example, the electronic handle 1100 of the cleaning device can be configured to dispense the fluid/composition from the at least one cartridge at a regulated pressure and/or dosage. In another example, mixing of two or more constituents from different cartridges can also take place in the handle 1100 to generate the fluid/composition that facilitates cleaning. Furthermore, the fluid/composition can comprise one or more cleaning agents/chemicals suitable for cleaning ear or nose of a user. For example, the handle 1100 can be configured to dispense/spray the fluid/composition from the cartridge in an electronic and regulated manner suitable for cleaning ear, for example, washing, anti-bacterial treatment, medicating, drug-delivery, coating, drying (the ear or the wax or the dirt), dissolving wax, softening wax, soaking, flushing, rinsing, or the like. FIGS. 30A-30B show different views of another version of the electronic handle 1100.

According to another embodiment of the invention, the electronic version of the handle 1100 can have a software and/or hardware capability to recognize, process and forward/receive information. Moreover, various functions and/or operating modes of the cleaning device can be implemented via simpler hardware or software configuration.

Figure 31:
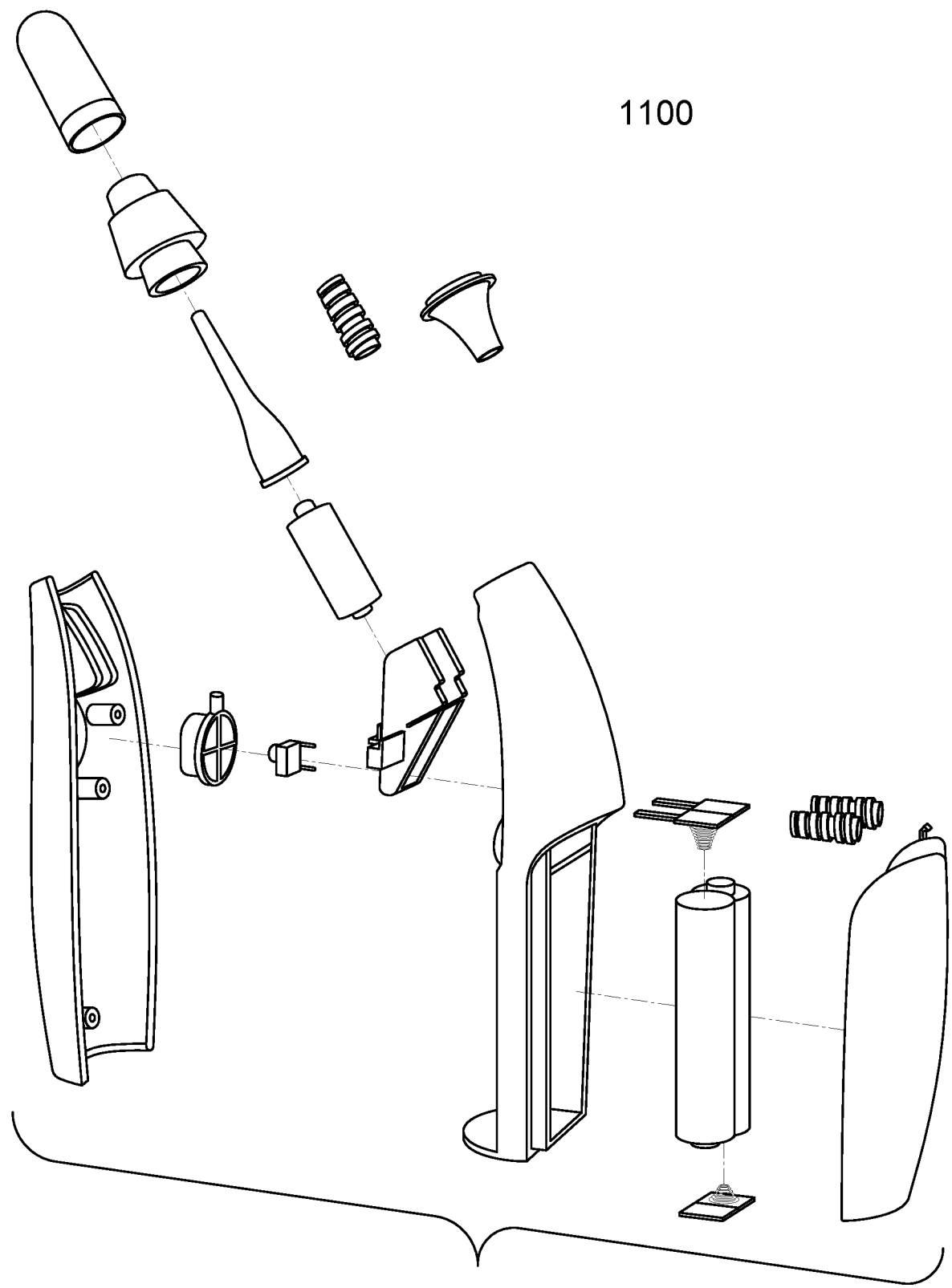

FIG. 31 shows an exploded view of the electronic version of the handle 1100.

Figure 32A:
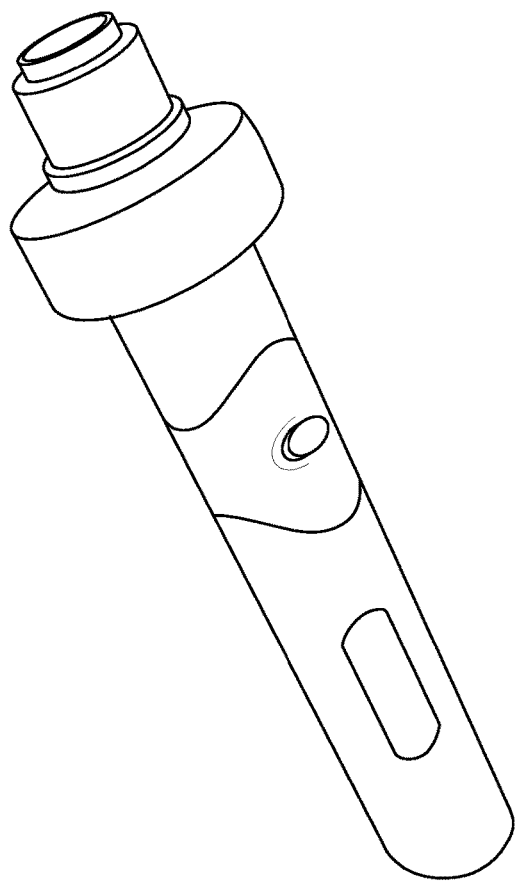
FIGS. 32A and 32B illustrate electronic versions of the handle1100 of the ear and/or nose cleaning device according to specific embodiment(s) of the present invention.
Figure 32B:
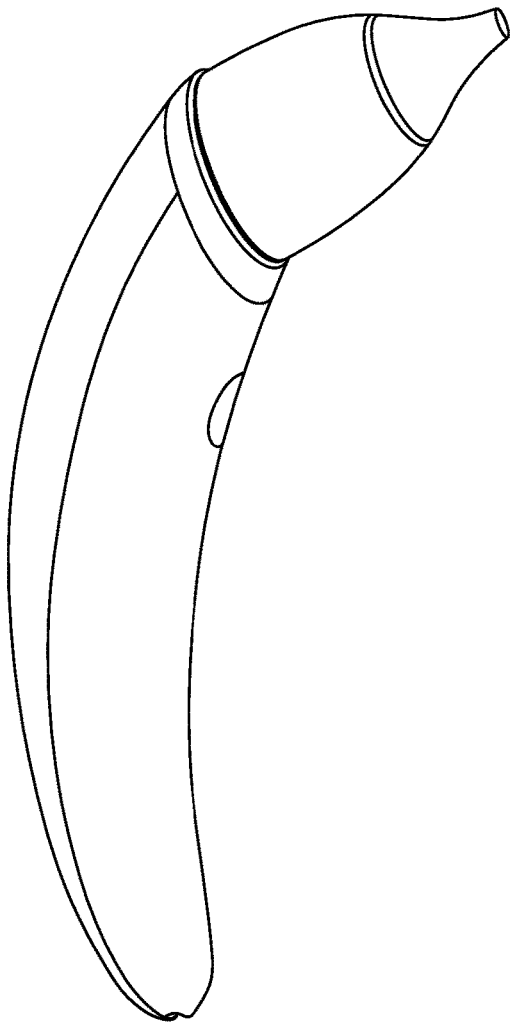

FIGS. 32A-32B show different versions of the electronic handle 1100.

It will be appreciated that the above description has described and illustrated specific embodiments and examples. However, the description is intended to cover any and all variations of various embodiments and examples of the invention. Combinations of the above embodiments/examples/arrangements not specifically described herein, will be apparent to those of skill in the art upon reviewing the above description. Therefore, it is intended that the disclosure not be limited to the particular embodiments/examples/arrangements disclosed, but that the invention will include all embodiments and arrangements falling within the scope of the appended claims.

I claim:

1. An ear, ear canal, and nose cleaning device comprising:
   a handle having a main body with sidewalls with at least a portion of said sidewalls transparent,
   an upper end with a top cover and selectively open lower end, and an interior including at least one cartridge stored therein;
   at least one cleaning tip stored within said at least one cartridge, the at least one cleaning tip having a generally spiral body;
   a connection mechanism to form a releasable connection between the handle and the at least one cleaning tip, said connection mechanism having
   a first connection interface on the handle,
   a second connection interface on the at least one cleaning tip to form the releasable connection between the handle and the at least one cleaning tip,
   a connection member having upper and lower sides and separable from said upper end and said at least one cleaning tip, the connection member including
   a downwardly depending collar extending from said lower side forming a third connection interface configured to engage operatively with the handle to form a first connection in a first direction,
   an upright centrally positioned shaft extending from said upper side,
   a plurality of nipples on said upper side, and
   an ejector to eject the at least one cleaning tip upon disengagement;
   wherein said shaft, plurality of nipples, and ejector form a fourth connection interface sized and shaped for insertion into a void within the spiral body of the at least one cleaning tip in a second direction;
   wherein said at least one cleaning tip is dispensed from said lower end by opening said lower end; and
   a stopper plate to limit insertion of the at least one cleaning tip into an ear or nose of a user, wherein at least one of position and size of the stopper plate is adjustable according to nostril size, ear canal size, or age group of the particular user.

2. The cleaning device of claim 1, wherein said spiral body has a hollow spoon shape feature disposed at a distal end of the at least one cleaning tip to facilitate cleaning.

3. The cleaning device of claim 1, wherein the handle includes a flat base to stand on a surface.

4. The cleaning device of claim 1, wherein the handle includes a bottom hole for hanging.

5. The cleaning device of claim 1, wherein the handle includes a tapered portion, a ribbed portion, or a combination thereof.

6. The cleaning device of claim 1, wherein the handle comprises a hollow space that acts as the at least one cartridge.

7. The cleaning device of claim 1, wherein the cleaning tip includes a flexible material and configured to engage operatively with said fourth connection interface.

8. The cleaning device of claim 1, wherein the spiral body is of a cylindrical shape arrangement sized for insertion into said ear canal.

9. The cleaning device of claim 1, wherein the at least one cartridge is configured to store one or more cleaning tips.

10. The cleaning device of claim 1, wherein at least one of the at least one cleaning tip, the cartridge and the connection mechanism is disposable.

* * * * *